(12) United States Patent
Kawwas et al.

(10) Patent No.: US 12,048,821 B2
(45) Date of Patent: Jul. 30, 2024

(54) DEVICES AND TECHNIQUES FOR CARDIOVASCULAR INTERVENTION

(71) Applicant: Medtronic Vascular, Inc., Santa Rosa, CA (US)

(72) Inventors: Jaclyn Kawwas, San Francisco, CA (US); Richard L. Klein, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 28 days.

(21) Appl. No.: 17/745,724

(22) Filed: May 16, 2022

(65) Prior Publication Data
US 2022/0273916 A1    Sep. 1, 2022

Related U.S. Application Data

(63) Continuation of application No. 16/657,630, filed on Oct. 18, 2019, now Pat. No. 11,357,958.
(Continued)

(51) Int. Cl.
*A61M 25/10*    (2013.01)
*A61F 2/24*    (2006.01)
*A61B 17/00*    (2006.01)

(52) U.S. Cl.
CPC ......... *A61M 25/104* (2013.01); *A61F 2/2433* (2013.01); *A61M 25/1002* (2013.01);
(Continued)

(58) Field of Classification Search
CPC ............ A61M 25/104; A61M 25/1002; A61F 2/2433; A61B 2017/00243; A61B 2017/00292; A61B 2017/00783
See application file for complete search history.

(56) References Cited

U.S. PATENT DOCUMENTS

| 7,803,168 B2 | 9/2010 | Gifford et al. |
| 8,574,247 B2 | 11/2013 | Adams et al. |

(Continued)

FOREIGN PATENT DOCUMENTS

| CN | 107261301 | 10/2017 |
| EP | 1415616 | 5/2004 |

(Continued)

OTHER PUBLICATIONS

PCT/US2019/057259, The International Search Report and the Written Opinion, mailed Mar. 17, 2020, 17 pgs.
(Continued)

*Primary Examiner* — Phong Son H Dang
(74) *Attorney, Agent, or Firm* — Medler Ferro Woodhouse & Mills PLLC

(57) ABSTRACT

Devices, assemblies, systems, and techniques described herein may deliver a pressure wave to structures of a heart, such an aortic valve. For example, a medical assembly may include an expandable member configured to expand from a collapsed configuration to an expanded configuration, the expandable member configured to at least partially define a channel through the expandable member in the expanded configuration and one or more electrodes carried by the expandable member. The one or more electrodes may be configured to transmit an electrical signal through a fluid to cause the fluid to undergo cavitation that generates a pressure wave within the fluid.

19 Claims, 19 Drawing Sheets

Related U.S. Application Data

(60) Provisional application No. 62/750,547, filed on Oct. 25, 2018.

(52) U.S. Cl.
CPC ............... *A61B 2017/00243* (2013.01); *A61B 2017/00292* (2013.01); *A61B 2017/00783* (2013.01)

(56) References Cited

U.S. PATENT DOCUMENTS

| | | | |
|---|---|---|---|
| 8,728,091 B2 | 5/2014 | Hakala et al. | |
| 8,956,371 B2* | 2/2015 | Hawkins | A61B 17/2202 601/4 |
| 9,011,463 B2 | 4/2015 | Adams et al. | |
| 9,034,025 B2* | 5/2015 | Sanati | A61F 2/954 623/1.11 |
| 9,044,618 B2 | 6/2015 | Hawkins et al. | |
| 9,072,534 B2* | 7/2015 | Adams | A61B 17/2202 |
| 9,220,521 B2 | 12/2015 | Hawkins et al. | |
| 9,554,815 B2 | 1/2017 | Adams | |
| 9,717,513 B2 | 8/2017 | Golan | |
| 9,730,715 B2 | 8/2017 | Adams | |
| 10,201,387 B2 | 2/2019 | Grace et al. | |
| 2005/0015048 A1 | 1/2005 | Chiu et al. | |
| 2006/0173475 A1 | 8/2006 | Lafontaine et al. | |
| 2009/0312768 A1 | 12/2009 | Hawkins et al. | |
| 2010/0094081 A1 | 4/2010 | Rothe et al. | |
| 2010/0324649 A1 | 12/2010 | Mattsson et al. | |
| 2011/0034832 A1 | 2/2011 | Cioanta et al. | |
| 2011/0264039 A1 | 10/2011 | Thielen et al. | |
| 2012/0109179 A1 | 5/2012 | Murphy et al. | |
| 2012/0116289 A1 | 5/2012 | Hawkins et al. | |
| 2012/0221013 A1 | 8/2012 | Hawkins et al. | |
| 2013/0060316 A1 | 3/2013 | Sanati et al. | |
| 2013/0085493 A1 | 4/2013 | Bloom et al. | |
| 2014/0025087 A1 | 1/2014 | Richardson | |
| 2014/0163592 A1 | 6/2014 | Hawkins et al. | |
| 2016/0184570 A1 | 6/2016 | Grace et al. | |
| 2016/0262784 A1 | 9/2016 | Grace et al. | |
| 2017/0265942 A1 | 9/2017 | Grace et al. | |
| 2018/0126127 A1 | 5/2018 | Devereux et al. | |
| 2018/0133443 A1 | 5/2018 | Osypka | |
| 2018/0153692 A1 | 6/2018 | Gerhardt et al. | |
| 2020/0129741 A1 | 4/2020 | Kawwas et al. | |

FOREIGN PATENT DOCUMENTS

| | | |
|---|---|---|
| WO | 2017070252 | 4/2017 |
| WO | 2018075924 | 4/2018 |

OTHER PUBLICATIONS

PCT/US2019/057249, The International Search Report and the Written Opinion, mailed Mar. 12, 2020, 18 pgs.
Communication Pursuant to Article 94(3) EPC, EP Application No. 19748494.1, mailed Feb. 15, 2023.
Communication Pursuant to Article 94(3) EPC, EP Application No. 19748494.1, mailed Dec. 22, 2023.
Notice on the First Office Action, CN Application No. 201980069321.8, mailed Apr. 11, 2024.

* cited by examiner

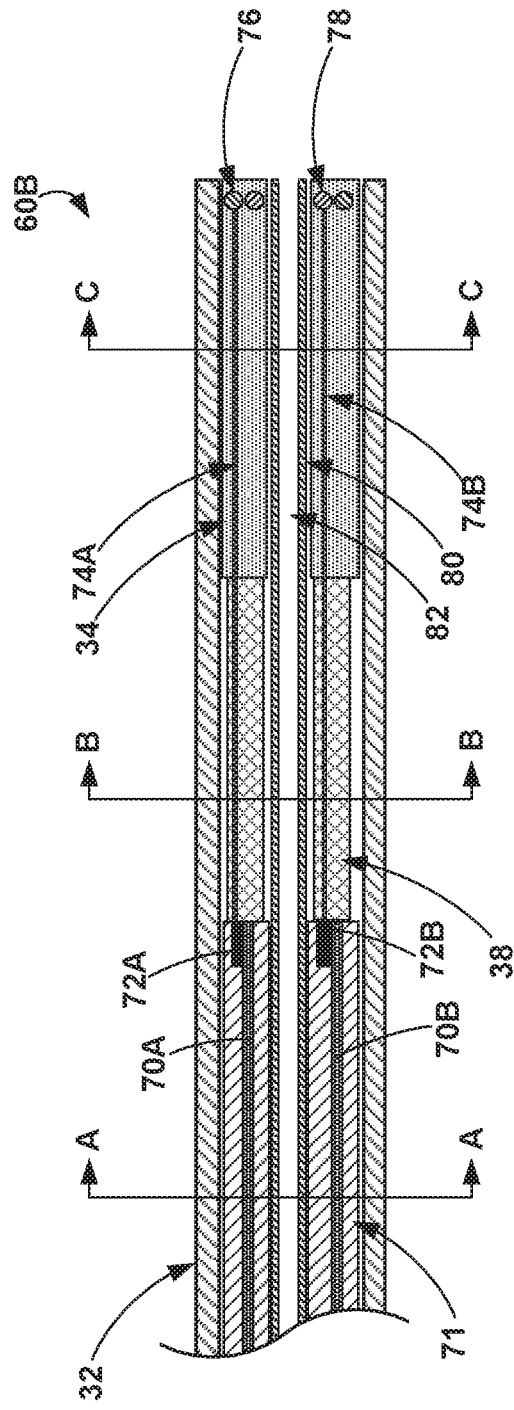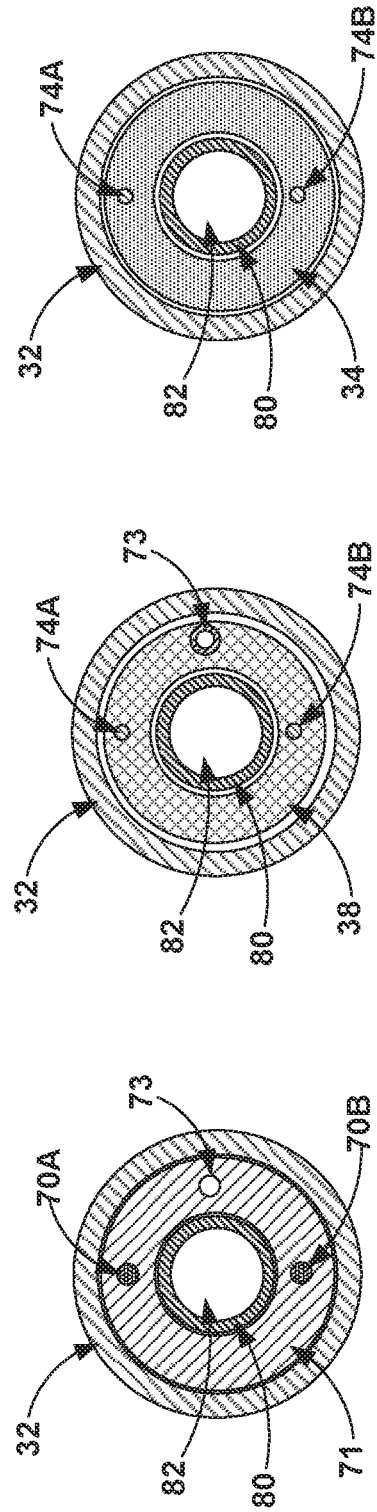
FIG. 5A
FIG. 5B
FIG. 5C
FIG. 5D

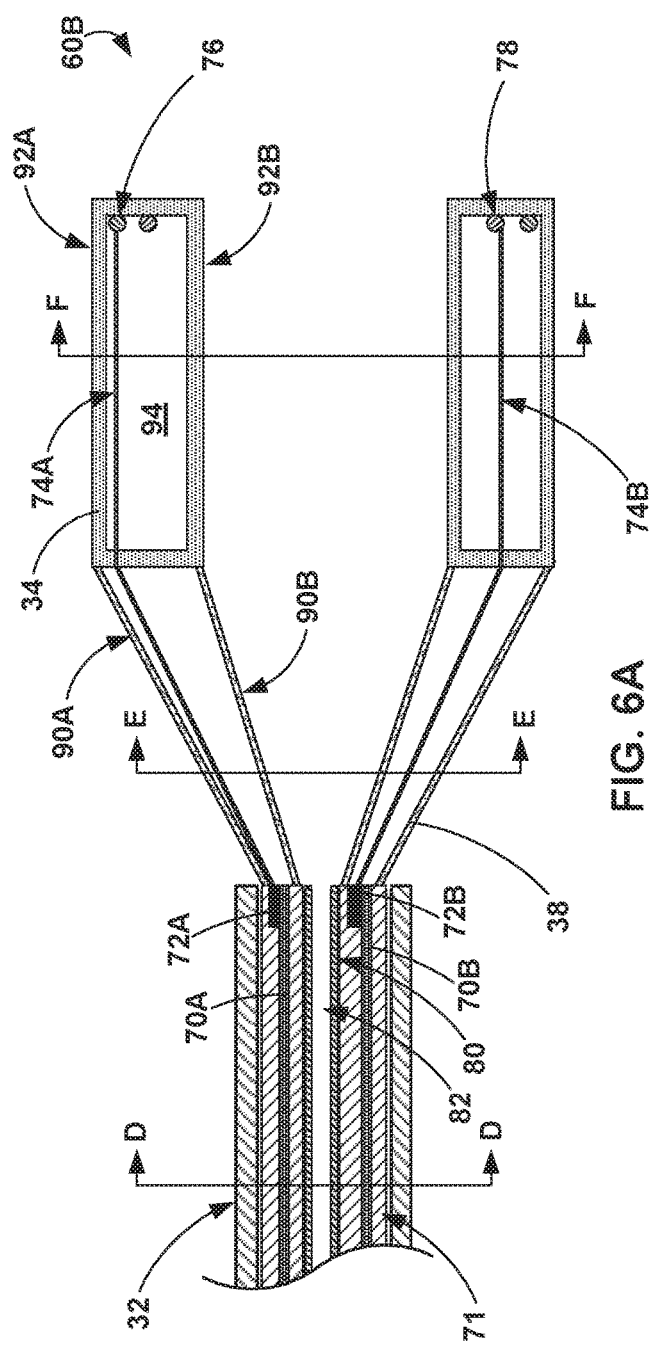
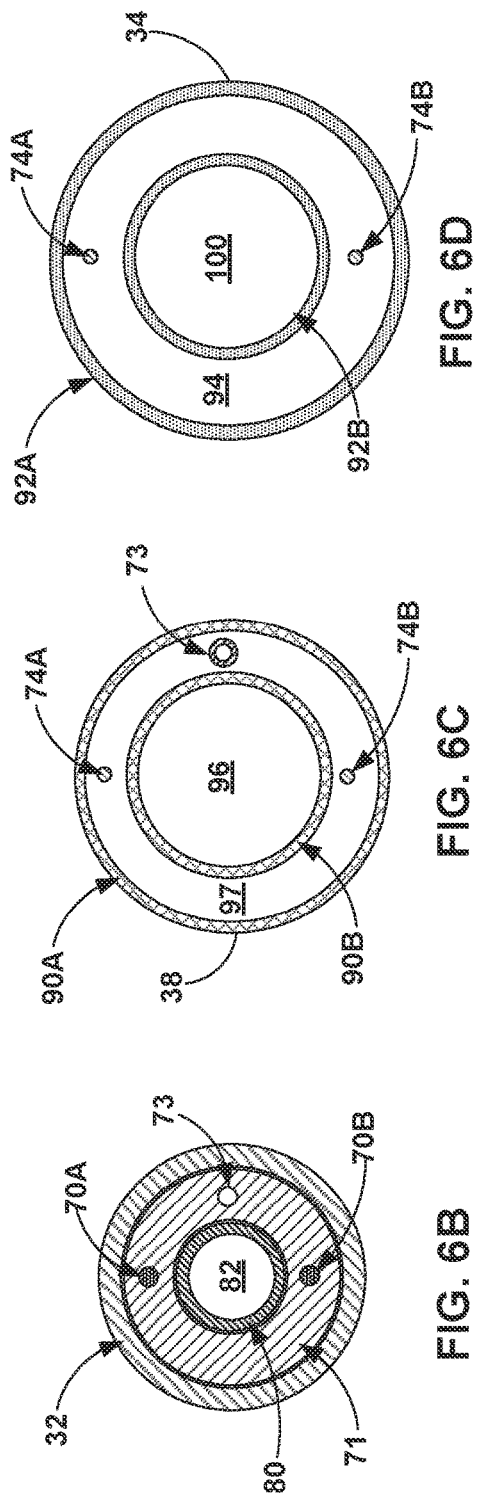
FIG. 6A
FIG. 6B
FIG. 6C
FIG. 6D

DEVICES AND TECHNIQUES FOR CARDIOVASCULAR INTERVENTION

CROSS REFERENCE TO RELATED APPLICATIONS

This application is a Continuation application of Ser. No. 16/657,630, filed Oct. 18, 2019, entitled "DEVICES AND TECHNIQUES FOR CARDIOVASCULAR INTERVENTION," now allowed, which claims the benefit of the filing date of U.S. Provisional Patent Application Ser. No. 62/750,547, filed Oct. 25, 2018, entitled "DEVICES AND TECHNIQUES FOR CARDIOVASCULAR INTERVENTION," which are herein incorporated by reference.

BACKGROUND

Patient conditions associated with heart valves such as, but not limited to, calcification, can produce a stenosis and/or valvular insufficiency or regurgitation. Valvular insufficiency or regurgitation occurs when a valve in a heart of a subject does not close completely, allowing blood to flow backwards (e.g., from the left ventricle to the left atrium), which may adversely impact the functionality of the heart. In some cases, valvular stenosis can cause the valve to become narrowed and hardened, which may prevent the valve from opening fully, thereby reducing blood flow through the valve. This reduced blood flow may cause the heart to work harder to pump blood through the diseased valve.

In some examples, a clinician may perform a medical procedure (e.g., a valvuloplasty) in which the clinician inserts a device, such as a balloon, into the valve and then expands the device to open the valve to a greater degree, which may promote greater blood flow through the valve. In addition, heart valve prostheses have been developed for repair and replacement of diseased and/or damaged heart valves. Some heart valve prostheses can be percutaneously delivered and deployed at the site of the diseased heart valve through a medical delivery system such as a catheter. An example of such a medical procedure is the transcatheter aortic valve replacement (TAVR) procedure. In some cases, a heart valve prosthesis includes an expandable stent to which tissue defining valves are mounted. The heart valve prostheses can be delivered while the stent is in a low-profile or collapsed configuration so that the stent is in a low-profile state for advancement through the patient's vasculature. Once positioned at the target treatment site, the stent can be expanded to engage native tissue at a target treatment site and position the heart valve prostheses at the target treatment site.

SUMMARY

In some aspects, this disclosure describes example medical assemblies, devices, systems, and techniques for treating cardiovascular structures (e.g., an aortic valve of a heart). For example, in one example, a medical assembly may include one or more expandable members configured to be expanded near and/or within a heart valve. In the expanded configuration, the one or more expandable members may define a channel. The medical assembly may include a catheter defining a lumen and configured to deliver a fluid (e.g., a contrast agent or other substance) through the lumen and channel defined by the one or more expandable members into the blood to enable imaging of cardiovascular structures. The one or more expandable members may also be configured to expand against leaflets of a valve to increase the opening of the valve (e.g., perform a valvuloplasty).

In another example, a medical assembly may include one or more expandable members that carry one or more electrodes configured to transmit an electrical signal through a fluid to cause the fluid to undergo cavitation that generates a pressure wave within the fluid. The cavitation of the fluid may be used treat a condition in a heart of a patient. For example, the cavitation may produce a high-energy pressure pulse wave that, when directed at a valvular stenosis, may be used to disrupt and fracture calcification partially or fully causing the valvular stenosis. In some examples, the disruption and fracture of the calcification may allow a portion of the valve, such as the leaflets of the valve, to move more freely and increase blood flow through the valve.

The one or more expandable members includes one or more balloons or other structures than can expand from a collapsible configuration within a catheter or outer sleeve. In some examples, the expandable member may be a balloon shaped as a torus that defines a channel, and the expandable member may carry the one or more electrodes, such as via electrodes within the expandable member or on an outer surface of the expandable member. After expanding the expandable member into the expanded configuration, the expandable member may dispose the carried one or more electrodes adjacent to, or within, the target valve for delivery of the pressure waves to the valve. In some examples, a contrast agent may be delivered into the blood vessel and/or heart through the channel defined by the one or more expandable members prior to and/or after treatment. The expandable member may expand within the valve to provide a force that assists in the enlargement of the valve opening, which may be provided after disruption and fracture of the calcification. In some examples, a heart valve prosthesis (e.g., a stent) may be delivered to a location of the cardiovasculature (e.g., a valve) through the channel in the expandable member to support a valve function after the disruption and fracture of the calcification allows the prosthesis to more easily and/or fully expanded in the valve, e.g., to achieve better patency of the vessel and achieve better blood flow through the vessel.

The following examples are disclosed herein. Example 1: A medical assembly comprising: at least one expandable member configured to expand from a collapsed configuration to an expanded configuration, the at least one expandable member configured to at least partially define a channel through the at least one expandable member in the expanded configuration; and a catheter defining a lumen and configured to deliver a fluid from the lumen and through the channel defined by the at least one expandable member in the expanded configuration, wherein the at least one expandable member is configured to reside within catheter in the collapsed configuration.

Example 2: the medical assembly of example 1, wherein the at least one expandable member is configured to deliver a radial force to leaflets of a valve in the expanded configuration to increase an opening of the valve.

Example 3: the medical assembly of any of examples 1 and 2, wherein the at least one expandable member is configured to expand to the expanded configuration via fluid delivered to an interior volume of the at least one expandable member.

Example 4: the medical assembly of any of examples 1 through 3, wherein the at least one expandable member comprises a torus shape in the expanded configuration, and wherein the channel is defined by an inner surface of the torus shape.

Example 5: the medical assembly of any of examples 1 through 4, wherein the at least one expandable member comprises two or more distinct expandable members that, in the expanded configuration, together define the channel.

Example 6: the medical assembly of any of examples 1 through 5, wherein: the lumen is a first lumen, the catheter defines a second lumen, the first lumen residing within the second lumen, and wherein the at least one expandable member is configured to reside within the second lumen in the collapsed configuration.

Example 7: the medical assembly of any of examples 1 through 6, further comprising a filter disposed proximal of the at least one expandable member in the expanded configuration, the filter configured to expand from a collapsed filter configuration to an expanded filter configuration.

Example 8: the medical assembly of example 7, wherein the filter is disposed proximal of the at least one expandable member and distal of a distal end a catheter that carries the filter and the at least one expandable member.

Example 9: the medical assembly of any of examples 1 through 8, wherein the filter comprises a conical shape in the expanded filter configuration, the conical shape having a distal filter diameter larger than a proximal filter diameter.

Example 10: the medical assembly of any of examples 1 through 9, further comprising one or more electrodes carried by the at least one expandable member, wherein the one or more electrodes are configured to transmit an electrical signal through a fluid to cause the fluid to undergo cavitation that generates a pressure wave within the fluid.

Example 11: the medical assembly of example 10, wherein the one or more electrodes are disposed within the at least one expandable member.

Example 12: the medical assembly of example 10, wherein the one or more electrodes are coupled to an exterior surface of the at least one expandable member.

Example 13: the medical assembly of example 10, further comprising: a first electrical conductor coupled to a first electrode of the one or more electrodes; a second electrical conductor coupled to a second electrode of the one or more electrodes; and an energy source configured to deliver the electrical signal between the first electrode and the second electrode via the first electrical conductor and the second electrical conductor.

Example 14: the medical assembly of any of examples 1 through 14, wherein the fluid comprises a contrast agent.

Example 15: a method comprising: expanding at least one expandable member from a collapsed configuration to an expanded configuration, the at least one expandable member configured to at least partially define a channel through the at least one expandable member in the expanded configuration; and delivering a fluid through a lumen defined by a catheter and through the channel defined by the at least one expandable member in the expanded configuration, wherein the at least one expandable member is configured to reside within catheter in the collapsed configuration.

Example 16: the method of example 15, further comprising delivering, with the at least one expandable member, a radial force to leaflets of a valve in the expanded configuration to increase an opening of the valve.

Example 17: the method of any of examples 15 and 16, wherein expanding the at least one expandable member comprises delivering a fluid to an interior volume of the at least one expandable member.

Example 18: the method of any of examples 15 through 17, wherein the at least one expandable member comprises a torus shape in the expanded configuration, and wherein the channel is defined by an inner surface of the torus shape.

Example 19: the method of any of examples 15 through 18, wherein the at least one expandable member comprises two or more distinct expandable members that, in the expanded configuration, together define the channel.

Example 20: the method of any of examples 15 through 19, wherein: the lumen is a first lumen, the catheter defines a second lumen, the first lumen residing within the second lumen, and wherein the at least one expandable member is configured to reside within the second lumen in the collapsed configuration.

Example 21: the method of any of examples 15 through 20, further comprising expanding a filter from a collapsed filter configuration to an expanded filter configuration, the filter disposed proximal of the at least one expandable member in the expanded configuration.

Example 22: the method of example 21, wherein the filter is disposed proximal of the at least one expandable member and distal of a distal end a catheter that carries the filter and the at least one expandable member.

Example 23: the method of example 21, wherein the filter comprises a conical shape in the expanded filter configuration, the conical shape having a distal filter diameter larger than a proximal filter diameter.

Example 24: the method of any of examples 15 through 23, further comprising transmitting, by one or more electrodes carried by the at least one expandable member, an electrical signal through a fluid to cause the fluid to undergo cavitation that generates a pressure wave within the fluid.

Example 25: the method of example 24, wherein the one or more electrodes are disposed within the at least one expandable member.

Example 26: the method of example 24, wherein the one or more electrodes are coupled to an exterior surface of the at least one expandable member.

Example 27: the method of any of examples 15 through 26, wherein the fluid comprises a contrast agent.

Example 28: a medical assembly comprising: at least one expandable member configured to expand from a collapsed configuration to an expanded configuration, the at least one expandable member configured to at least partially define a channel through the at least one expandable member in the expanded configuration; and one or more electrodes carried by the at least one expandable member, wherein the one or more electrodes are configured to transmit an electrical signal through a fluid to cause the fluid to undergo cavitation that generates a pressure wave within the fluid.

Example 29: the medical assembly of example 28, wherein the at least one expandable member comprises a torus shape in the expanded configuration, and wherein the channel is defined by an inner surface of the torus shape.

Example 30: the medical assembly of any of examples 28 and 29, wherein the one or more electrodes comprises a plurality of electrodes carried by the at least one expandable member.

Example 31: the medical assembly of example 30, wherein the plurality of electrodes is configured to transmit the electrical signal between at least two electrodes of the plurality of electrodes.

Example 32: the medical assembly of example 30, wherein the plurality of electrodes is disposed at a distal end of the at least one expandable member.

Example 33: the medical assembly of example 30, wherein the plurality of electrodes comprises at least two concentric ring electrodes.

Example 34: the medical assembly of any of examples 28 through 33, wherein the one or more electrodes are disposed within the expandable member.

Example 35: the medical assembly of any of examples 28 through 34, wherein the one or more electrodes are coupled to an exterior surface of the expandable member.

Example 36: the medical assembly of any of examples 28 through 35, wherein the one or more electrodes are constructed of at least one of nitinol, stainless steel, platinum, platinum-iridium, gold, tantalum, or tungsten.

Example 37: the medical assembly of any of examples 28 through 36, further comprising a filter disposed proximal of the at least one expandable member in the expanded configuration, the filter configured to expand from a collapsed filter configuration to an expanded filter configuration.

Example 38: the medical assembly of any of examples 28 through 37, wherein the filter is disposed proximal of the at least one expandable member and distal of a distal end a catheter that carries the filter and the at least one expandable member.

Example 39: the medical assembly of any of examples 28 through 38, wherein the filter comprises a conical shape in the expanded filter configuration, the conical shape having a distal filter diameter larger than a proximal filter diameter.

Example 40: the medical assembly of any of examples 28 through 39, further comprising: a first electrical conductor coupled to a first electrode of the one or more electrodes; a second electrical conductor coupled to a second electrode of the one or more electrodes; and an energy source configured to deliver the electrical signal between the first electrode and the second electrode via the first electrical conductor and the second electrical conductor.

Example 41: the medical assembly of any of examples 28 through 41, further comprising a catheter defining a lumen, wherein the at least one expandable member is configured to reside within lumen in the collapsed configuration, and wherein the one or more electrodes are configured to reside within the lumen along with the at least one expandable member in the collapsed configuration.

Example 42: the medical assembly of example 41, wherein the lumen comprises a first lumen, and wherein the catheter defines a second lumen different than the first lumen, and wherein the second lumen is configured to deliver contrast agent through the lumen and the channel of the at least one expandable member in the expanded configuration.

Example 43: the medical assembly of any of examples 28 through 42, further comprising an electrode separate from the at least one expandable member, wherein the electrical signal is transmitted between the one or more electrodes carried by the at least one expandable member and the electrode separate from the at least one expandable member.

Example 44: the medical assembly of example 43, further comprising a guidewire carrying the electrode separate from the at least one expandable member.

Example 45: a medical assembly comprising: a catheter defining a lumen; an expandable member configured to expand from a first collapsed configuration within the lumen to a first expanded configuration distal of the lumen, the expandable member configured to at least partially define a channel through the expandable member in the expanded configuration; one or more electrodes carried by the expandable member, wherein the one or more electrodes are configured to transmit an electrical signal through a fluid to cause the fluid to undergo cavitation that generates a pressure wave within the fluid; and a filter disposed proximal of the expandable member in the expanded configuration, the filter configured to expand from a second collapsed configuration to a second expanded configuration.

Example 46: the medical assembly of example 45, wherein the filter comprises a conical shape in the second expanded configuration, the conical shape having a distal filter diameter larger than a proximal filter diameter.

Example 47: the medical assembly of example 46, wherein a distal end of the filter is attached to a proximal end of the expandable member, and wherein a proximal end of the filter is attached to the catheter.

Example 48: the medical assembly of any of examples 45 through 47, wherein the filter comprises a nitinol mesh.

Example 49: the medical assembly of any of examples 45 through 48, wherein the expandable member comprises a torus shape in the first expanded configuration, and wherein the channel is defined by an inner surface of the torus shape.

Example 50: the medical assembly of any of examples 45 through 49, wherein the lumen comprises a first lumen, and wherein the catheter defines a second lumen configured as an inflation lumen coupled to the expandable member.

Example 51: the medical assembly of any of examples 45 through 50, wherein the one or more electrodes comprises at least two concentric ring electrodes.

Example 52: a method comprising: expanding at least one expandable member from a collapsed configuration to an expanded configuration, the at least one expandable member configured to at least partially define a channel through the at least one expandable member in the expanded configuration; and transmitting, via one or more electrodes carried by the at least one expandable member, an electrical signal through a fluid to cause the fluid to undergo cavitation that generates a pressure wave within the fluid.

The details of one or more examples are set forth in the accompanying drawings and the description below. Other features, objects, and advantages of examples according to this disclosure will be apparent from the description and drawings, and from the claims.

BRIEF DESCRIPTION OF DRAWINGS

FIG. 5A is a cross-sectional view of the distal end of the example catheter of FIG. 4 when the example expandable member is in the collapsed configuration.

FIGS. 5B, 5C, and 5D are cross-sectional views of different axial positions along the catheter of FIG. 5A.

FIG. 6A is a cross-sectional view of the distal end of the example catheter of FIG. 4 when the example expandable member is in the expanded configuration.

FIGS. 6B, 6C, and 6D are cross-sectional views of different axial positions along the catheter of FIG. 6A.

DETAILED DESCRIPTION

Figure 1A:
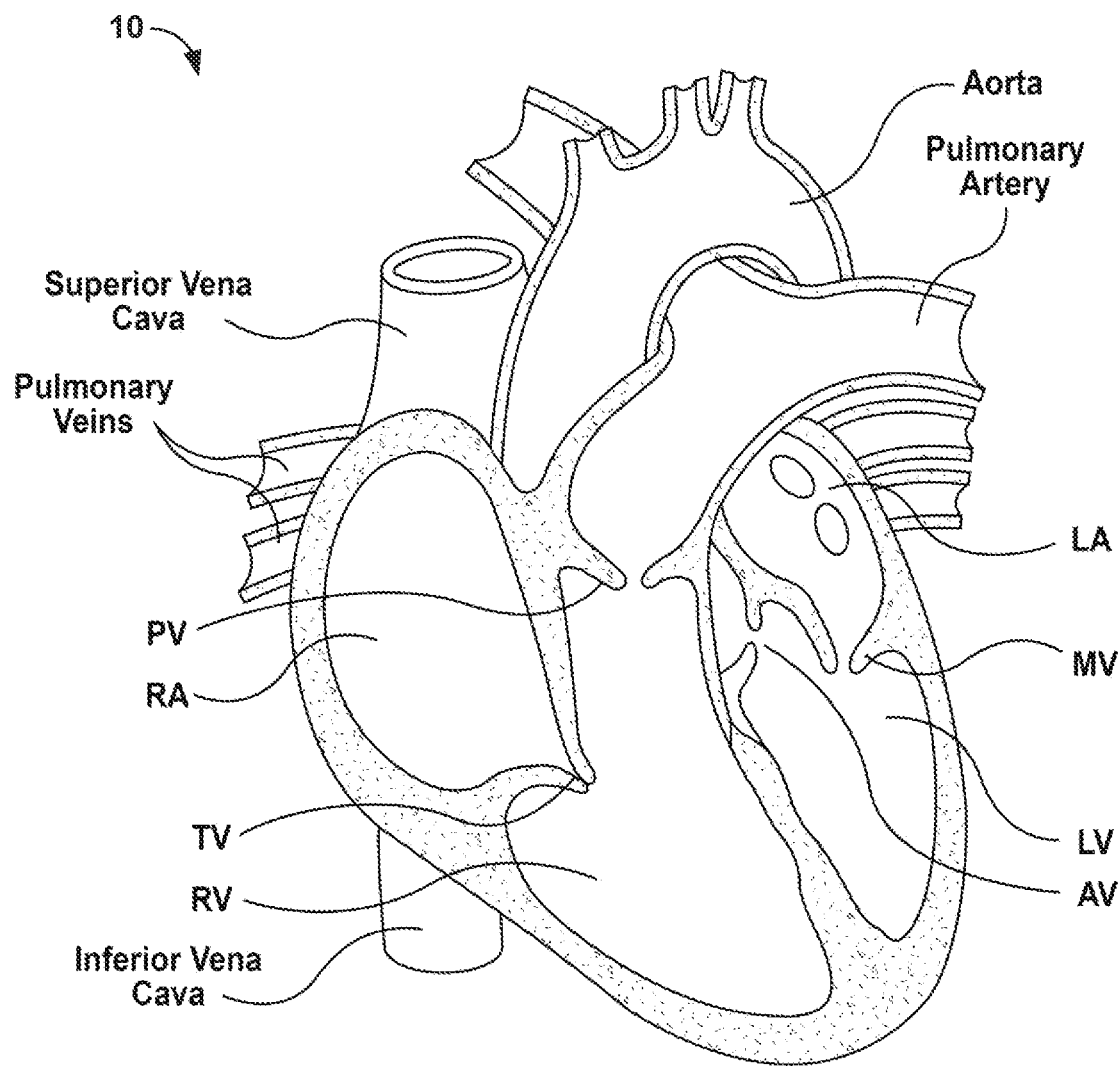
FIGS. 1A and 1B are schematic cross-sectional views of an example human heart.

This disclosure describes medical assemblies, devices, systems, and techniques for treating a patient, such as increasing heart valve function and/or reducing and/or disrupting calcification on valves of the heart. Over time, tissues in the cardiovascular system can develop one or more conditions that affects blood flow (e.g., reduce blood flow and/or change direction of some blood flow to or from the heart). For example, a target treatment site may be a portion of a heart valve, such as an aortic valve or mitral valve, that includes a calcified lesion, e.g., calcified plaque buildup on or within at least a portion of the valve. These calcified lesions may develop around the periphery of the valve and/or on the leaflets designed to move within the valve. The calcium buildup may occur with age as the heart valves accumulate deposits of calcium which is a mineral found the blood. As blood repeatedly flows over the affected valve, deposits of calcium can build up on or within the leaflets or cusps of the valve, resulting in a stiffening (e.g., reduced pliability) of the leaflets. This stiffening may narrow the opening of the valve, creating a stenosis that can result in adverse physiological effects to the patient. These calcified lesions may be more prevalent in high pressure areas around the heart, such as the mitral valve or aortic valve associated with the left ventricle.

In some examples, a balloon or other device may be used to mechanically open leaflets of a valve in a procedure referred to as valvuloplasty. However, typical balloons used occlude blood flow out from the valve during the procedure. In addition, if a clinician desires to deliver contrast agent to the blood in the treatment site to facilitate imaging of cardiovascular structures (e.g., fluoroscopy or computed topography (CT) imaging), the clinician needs to use a second access point—different from the balloon—in the patient to navigate the contrast agent catheter to the site.

Calcified lesions in the cardiovasculature may be very hard (e.g., relative to a native valve or blood vessel) and difficult to treat using traditional methods, such as balloon angioplasty, stenting, thrombectomy, atherectomy, valvuloplasty, or other interventional procedures. Even with the introduction of a heart valve prosthesis, the calcification of the heart valve may create a hinderance to alleviating the stenosis and returning the heart valve to normal flow parameters previous to the development of the calcification. For example, the calcification may reduce the elasticity of the native heart valve, which may interfere with the ability of a prosthetic heart valve that is implanted proximate to or within an annulus of the native heart valve to expand a desirable amount and define a desired flow diameter (e.g., flow rate and/or pressure through the heart valve).

As described herein, an expandable member may be configured to expand from a collapsed configuration to an expanded configuration. The expandable member may include one or more balloons or other structures that can expand as described herein. The expandable member may define a channel. For example, blood can flow through the channel while the expandable member is expanded within the vasculature. In addition, the medical assembly may be configured to deliver contrast agent through a lumen of a catheter carrying the expandable member and the channel defined by expandable member to facilitate imaging of structures within the patient during the procedure. In this manner, example medical assemblies herein may improve blood flow and imaging possibilities during valvuloplasty procedures.

In some examples, the expandable member may carry one or more electrodes (e.g., electrodes disposed within the expandable member and/or on an exterior surface of the expandable member), wherein the one or more electrodes are configured to transmit an electrical signal to a fluid, such as a fluid contained within the expandable member (or heart or vasculature of the patient, depending on the location of the electrodes). The energy transmitted to the fluid may rapidly heat the fluid to produce a short-lived gaseous steam/plasma bubble within the fluid that quickly collapses (e.g., cavitates), releasing energy in the form of a pressure pulse wave. The pulse wave may be used to treat a defect in the heart or vasculature of the patient at a target treatment site.

In some examples, a cavitation procedure using the expandable member and medical assemblies described herein may be performed in the fluid adjacent to one or more calcified lesions to produce pressure pulse waves within the fluid. The pressure pulse waves resulting from the cavitation may impact a calcified lesion (or other defect) at a target treatment site to fracture or disrupt at least part of the lesion. For example, the pressure pulse waves may fracture or disrupt at least a portion of a calcified lesion on a leaflet of a heart valve (e.g., the aortic valve or mitral valve). Following the cavitation, the tissue at the target treatment site (e.g., heart valve) may be more easily expanded than prior to the cavitation. For example, the expandable member, or a different balloon or stent, for example, may be inserted into the treated valve and expanded to expand the opening in the valve to enable a larger flow diameter than previously possible with the calcified lesion(s). In examples in which the expandable member is used to treat calcification on the leaflets of a heart valve, post-cavitation, the calcified leaflets may become more elastic, allowing for easier manipulation when deploying the expandable member, a different balloon, or a stent within the valve. In addition, the more elastic native leaflets may better enable a stent of a prosthetic heart valve to expand more fully in place proximate to or within an annulus of the native heart valve, which may help prevent valvular leakage in the future.

Delivering the cavitation treatment via an expandable member as described herein may provide one or more advantages. For example, the expandable member may be configured to direct pressure pulse waves against the surfaces of one or more leaflets of a heart valve to remove a greater amount of calcification. In some examples, the expandable member may define a channel in the expanded configuration such that contrast agent may be delivered into the blood stream through the channel, which may enable imaging the valve and surrounding vasculature without insertion of a separate catheter to deliver the contrast agent. In some examples, the expandable member itself may be expanded within the valve after cavitation in order to force the leaflets open and perform valvuloplasty on the target heart valve. In some examples, the catheter may define an inner lumen such that a heart valve prosthesis can be deployed through the inner lumen and the channel within the expandable member and implanted over the target valve. Each of these procedures, alone or in any combination, may improve treatment efficacy, reduce procedure duration, reduce patient recovery, and/or reduce the number of medical devices needed to be inserted into the patient during a medical procedure. Reducing the number of devices that are introduced into a patient to provide treatment may help reduce the amount of time required for a medical procedure, thereby reducing the amount of radiation the patient and clinician may be exposed to during the medical procedure, may reduce treatment cost by reducing the number of vasculature access devices (e.g., needle, introducer sheath, and the like) used to perform the medical procedure, may reduce the post procedure recovery time for the patient, or any combination thereof.

Although heart valves are generally described herein as example target tissue sites to be treated, the medical assemblies described herein may be configured to treat other types of tissues in other locations of the body in other examples. For example, an expandable member may be configured to reduce calcified lesions on a chamber wall in the heart or on the inner surface of blood vessels, including larger arteries. Although human structures are described herein, other animal species may be treated using the medical assemblies and techniques described herein.

Figure 1B:
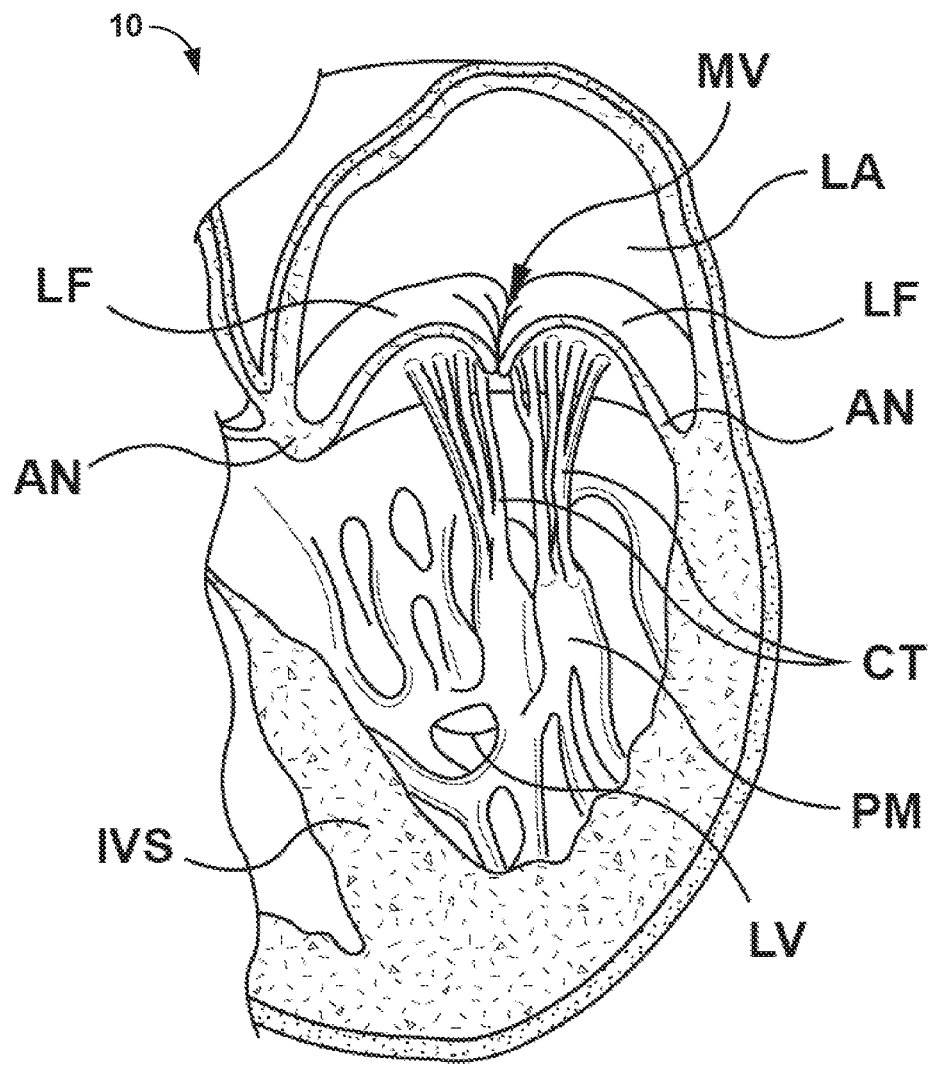

FIGS. 1A and 1B are schematic cross-sectional views of an example human heart 10. The human heart 10 is a four chambered, muscular organ that provides blood circulation through the body during a cardiac cycle. The four main chambers include the right atrium (RA) and right ventricle (RV) which supplies the pulmonary circulation, and the left atrium (LA) and left ventricle (LV) which supplies oxygenated blood received from the lungs to the remaining body. To ensure that blood flows in one direction through the heart, atrioventricular valves (tricuspid valve (TV) and mitral valves (MV)) are present between the junctions of the atrium and the ventricles, and semi-lunar valves (pulmonary valve (PV) and aortic valve (AV)) govern the exits of the ventricles leading to the lungs and the rest of the body. These valves contain leaflets (LF) or cusps that open and shut in response to blood pressure changes caused by the contraction and relaxation of the heart chambers. FIG. 1B is a schematic sectional illustration of a left ventricle LV of heart 10 showing anatomical structures and a native mitral valve MV.

The left atrium LA receives oxygenated blood from the lungs via the pulmonary veins and pumps the oxygenated blood through the mitral valve MV and into the left ventricle LV during ventricular diastole. The left ventricle LV contracts during systole and blood flows outwardly through the aortic valve AV, into the aorta and to the remainder of the body. In a healthy heart, the leaflets LF of the native mitral valve MV meet evenly at the free edges or "coapt" to close and prevent back flow of blood into the left atrium LA during contraction of the left ventricle LV. The tissue of the leaflets LF attach to the surrounding heart structure via a dense fibrous ring of connective tissue called an annulus AN. The flexible tissue of the leaflets LF of the native mitral valve MV are connected to papillary muscles PM, which extend upwardly from the lower wall of the left ventricle LV and the interventricular septum IVS, via branching tendons called chordae tendinae CT. In a heart 10 having a calcified plaque buildup, the leaflets LF of the valves (e.g., aortic valve AV or mitral valve MV) may harden and may not sufficiently coapt or meet, such that regurgitation may occur where the valve does not close completely, allowing blood to flow backwards (e.g., from the left ventricle LV to the left atrium LA). The left side of heart 10 (e.g., mitral valve MV and aortic valve AV) can be more likely to become calcified because of the higher pressures generated by the left ventricle LV. Performing a valvuloplasty (e.g., physically pushing the leaflets LF open by a balloon) and/or the introduction of a heart valve prostheses may address some of the inefficiencies of the leaflets LF but may have little or no effect on reducing the calcified buildup or alleviating the stenosis caused by the buildup. In addition, in some examples, a heart valve prosthesis may present undesirable side effects such as paravalvular leaking (PVL) and/or the need for short term or permanent artificial pacing of the heart (e.g., via an implanted pacemaker).

The medical assemblies described herein may be used to treat such calcified plaque buildup on or within a heart valve by cavitating the fluid in the vessel or portion of the heart to generate pressure pulse waves within the fluid to mechanically fracture or dislodge the calcifications. Once fractured or dislodged via cavitation, the tissues of the targeted treatment site may be more easily expanded to a normal flow diameter or function as opposed to tissues not exposed to cavitation therapy.

In some examples, the delivery catheters and methods are presented for the treatment of such heart valves as part of a procedure for minimally invasive valvuloplasty and/or implantation of a stent such as a stent that forms part of an artificial or prosthetic heart valve). For example, in accordance with the examples described below, the medical assemblies described herein can be used to percutaneously direct and deliver a mitral or aortic valve prosthesis via an intravascular retrograde approach.

Figure 2A:
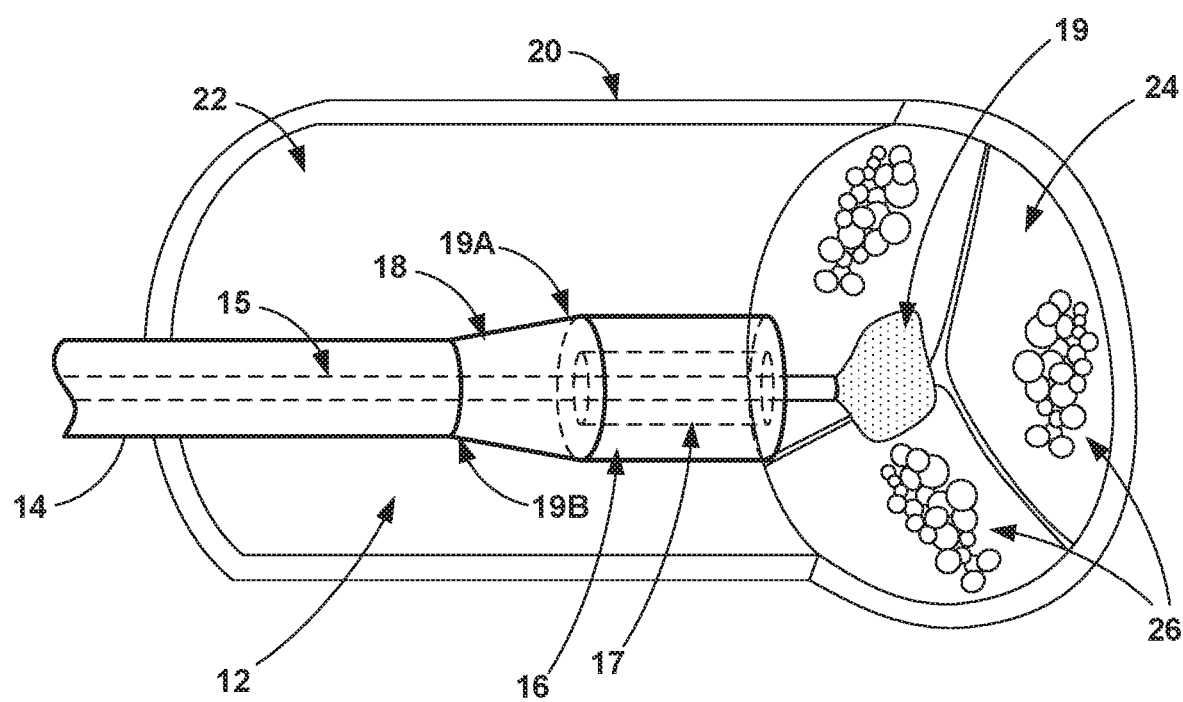
FIG. 2A is a conceptual view of an example medical assembly configured to deliver contrast agent into a portion of a vessel.

FIG. 2A is a conceptual view of an example medical assembly 12 configured to deliver a fluid, such as contrast agent 19, into a portion of the cardiovasculature. As shown in the example of FIG. 2A, aortic valve 24 includes three leaflets and is disposed upstream from aorta 20. As discussed above, one or more leaflets of aortic valve 24 may have reduced functionality (e.g., reduced movement of the leaflets), which may be at least partially due to the presence of calcified lesions 26 on each of the leaflets. In order to treat aortic valve 24, medical assembly 12 may be inserted through lumen 22 within aorta 20.

Medical assembly 12 includes expandable member 16 configured to expand from a collapsed configuration (not shown in FIG. 2A) to an expanded configuration (shown as a partially expanded configuration in FIG. 2A). The collapsed configuration may enable expandable member 16 and the distal end of medical assembly 12 to navigate the vasculature and/or other narrow spaces in order to reach the target treatment site. Expandable member 16 in the collapsed configuration may be advanced out from catheter 14 to assume the expanded configuration. Expandable member 16 may also be configured to at least partially define channel 17 through expandable member 16 in the expanded configuration. For example, expandable member 16 may define a torus shape, wherein the radially inward facing surface of the torus defines channel 17. In some examples, expandable member 16 may be a balloon that is inflated with a fluid. For example, catheter 14 may define a lumen or include another inner catheter that is configured as an inflation lumen coupled to expandable member 16 and configured to deliver a fluid to expand expandable member 16. In other examples, expandable member 16 may be an expandable structure formed of an expandable frame, such as an expandable metal frame, which may be covered by a fluid permeable member in some examples. Although expandable member 16 is shown as a single structure in the example of FIG. 2A, two or more expandable members may define a channel such as channel 17 in other examples.

Figure 2B:
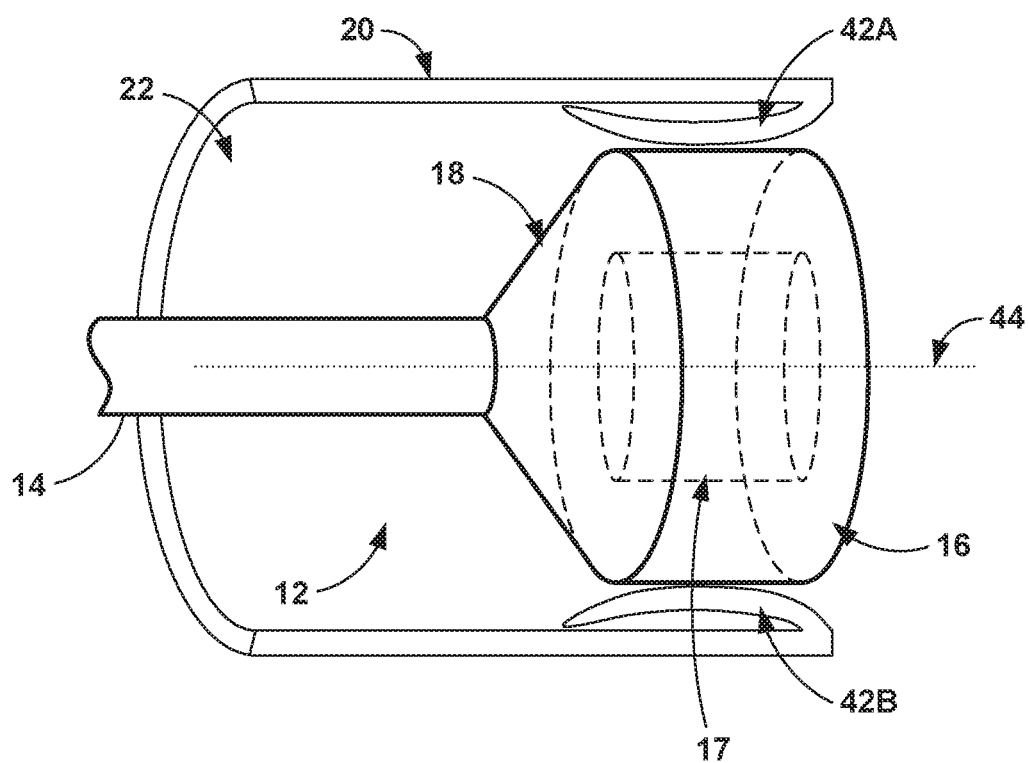
FIG. 2B is a conceptual view of the example medical assembly of FIG. 2A configured to apply a force to leaflets of a heart valve and increase a size of the opening of the heart valve.

Medical assembly 12 may also include filter 18 disposed proximal of expandable member 16 in the expanded configuration. Filter 18 may be sized such that blood constituents (e.g., plasma, red blood cells, white blood cells, platelets, and the like) pass through the pores in filter 18 and most if not all of the fragments of calcified lesion do not pass filter 18 during a procedure, such as shown in FIG. 2B. In some examples, filter 18 may be formed from a polymer such as polyethylene terephthalate (PET), polyethylene (PE), polyether block amide (e.g., Pebax©), or nylon, a metal mesh, or any combination thereof. In some examples, the porosity of the material of filter 18, such as a polymer, may be created laser drilling holes in the material.

Filter 18 may be configured to expand from a collapsed filter configuration (not shown in FIG. 2A) when stored within catheter 14 to an expanded filter configuration as shown in FIG. 2B. Filter 18 may define a conical shape in the expanded filter configuration, where the conical shape has a distal filter diameter larger than a proximal filter diameter. However, other shapes for filter 18 are possible and may be determined by one or more portions of expandable member 16 to which filter 18 is attached. The distal end 19A of filter 18 (e.g., the end of filter 18 closer to expandable member 16) may be coupled to the proximal end of expandable member 16, and the proximal end 19B (e.g., the end of filter 18 furthest from expandable member 16) of filter 18 may be coupled to catheter 14 or a structure within catheter 14, for example. In some examples, filter 18 may be constructed of a nitinol mesh or other material that can reside in the collapsed configuration and then be expanded out from catheter 14. As shown in FIG. 2A, filter 18 may be partially expanded.

Expandable member 16 may be one or more balloons in some examples, and the one or more balloons may be formed from any suitable material, such as a flexible polymeric material that is configured to form a tight seal with catheter 14 or a different elongated member within catheter 14. In some examples, expandable member 16 may be formed physically separate from catheter 14 and attached to an exterior surface or interior surface of an inner elongated member via co-extrusion, bonding, adhesives, or the like. In other examples, expandable member 16 may be integrally formed with an inner elongated member such that expandable member 16 is embedded or at least partially embedded in the inner elongated member. In other examples, expandable member 16 may be separated from an inner elongated member such that expandable member 16 forms a tight seal with itself.

Expandable member 16 may be constructed using a flexible polymeric material including, for example, nylon 12, polyethylene, polyethylene terephthalate (PET), silicone, polyvinyl chloride, polypropylene, polyurethanes, polyamides, polyesters, latex, natural rubber, synthetic rubber, polyether block amides, or the like. Additionally, or alternatively expandable member 16 may be constructed with an electrically insulative material and/or an electrically conductive material.

In some examples, expandable member 16 may be configured to be deflatable via a vacuum or other stable source to forcibly remove fluid from the balloon, thereby allowing for quicker collapse and/or a lower cross-sectional profile after the cavitation procedure is completed. Additionally, or alternatively, expandable member 16 may include one or more perfusion ports allowing fluid to continuously flow from the expandable member 16 into the vessel or heart of the patient.

Expandable member 16 may have any suitable size or shape. In some examples, expandable member 16 may define a cross sectional diameter of about 10 mm to about 50 mm in the expanded configuration so that expandable member 16 may be deployed in the fully expanded configuration within aortic valve 24 after the cavitation procedure, e.g., to contact and expand aortic valve 24 as part of a valvuloplasty procedure. Expandable member 16 may also have any suitable length (e.g., measured along longitudinal axis 44). For some procedures used to treat calcifications in or near a heart valve (e.g., aortic valve 24) of a patient, expandable member 16 may define a length of about 15 mm to about 80 mm.

In some examples, catheter 14 may define or include multiple lumens. For example, catheter 14 may define a first lumen within which filter 18 and/or expandable member 16 may reside in the collapsed configurations and a second lumen configured to deliver contrast agent through the second lumen and channel 17 of expandable member 16 in the expanded configuration. As shown in FIG. 2A, elongated member 15 may inserted within the second lumen and configured to deliver contrast agent through channel 17 of expandable member 16 and into the blood stream. However, in other example, contrast agent may be delivered directly through the second lumen instead of elongated member 15 passing through the second lumen. In some examples, medical assembly 12 may facilitate contrast agent delivery multiple times during a procedure, such as before, during, and/or after a valvuloplasty. In this manner, medical assembly 12 may be configured to deliver contrast agent into the blood stream without another catheter being inserted at a point separate from that of catheter 14. Imaging of the vasculature (e.g., via computed tomography, magnetic resonance imaging, or fluoroscopy) with contrast agent may aid the clinician in directing expandable member 16 to the appropriate location of valve 24 to perform a valvuloplasty as shown in FIG. 2B, and/or deliver a prosthetic valve to valve 24, for example. Although contrast agent 19 is described herein, other fluids may alternatively or additionally be delivered through lumen 15 and channel 17. For example, these other fluids may include agents such as anti-inflammatories to the tissue, hydrolyzing agents for dissolving calcium on tissue, or any other substances that may facilitate or aid in the procedures described herein.

FIG. 2B is a conceptual view of the example medical assembly 12 of FIG. 2A configured to apply a force to leaflets 42A and 42B (collectively "leaflets 42") of a heart valve 24 and increase a size of the opening of heart valve 24. As shown in FIG. 2B, expandable member 16 may be used to physically increase the size of the opening of a heart valve (e.g., aortic valve 24) by mechanically forcing leaflets 42 radially outward from axis 44.

When expandable member 16 is at least partially collapsed (shown in FIG. 2A), expandable member 16 may be advanced to a position at least partially within heart valve 24. Once positioned within the heart valve, expandable member 16 may be expanded into the expanded configuration as shown in FIG. 2B. This expansion produces a radial force away from longitudinal axis 44 and against the surface of leaflets 42. As expandable member 16 continues to expand, expandable member 16 forces leaflets 42 towards the outer edge of heart valve 24 to increase the size of the opening of heart valve 24 and increase blood flow. This portion of the procedure may be referred to as a valvuloplasty. During this procedure, blood may continue to pass through channel 17 and filter 18. After the valvuloplasty, in some examples, a clinician may insert a heart valve prosthesis through a lumen in catheter 14 and channel 17 and into the native valve 24. Once these procedures are complete, expandable member 16 and filter 18 may be collapsed and retracted within catheter 14 for removal from the patient via the artery insertion location.

In some cases, the calcification of calcified lesions 26 may not release into a blood stream of a patient. In other cases, however, at least some calcification may break away from lesions 26 and create emboli that releases into a blood stream of a patient. An embolic protection element, e.g., filter 18, is positioned downstream of the target treatment site to collect emboli and any portions of calcified lesions 26 that may be dislodged during the valvuloplasty. The embolic protection element can be any suitable device, including, but not limited to, a blood permeable membrane or wire mesh mechanically connected to an elongated member. Although filter 18 or an embolic protection element may be shows as coupled to catheter 14, filter 18 or the embolic protection element may be carried by or otherwise attached to a different elongate member in other examples.

Figure 3A:
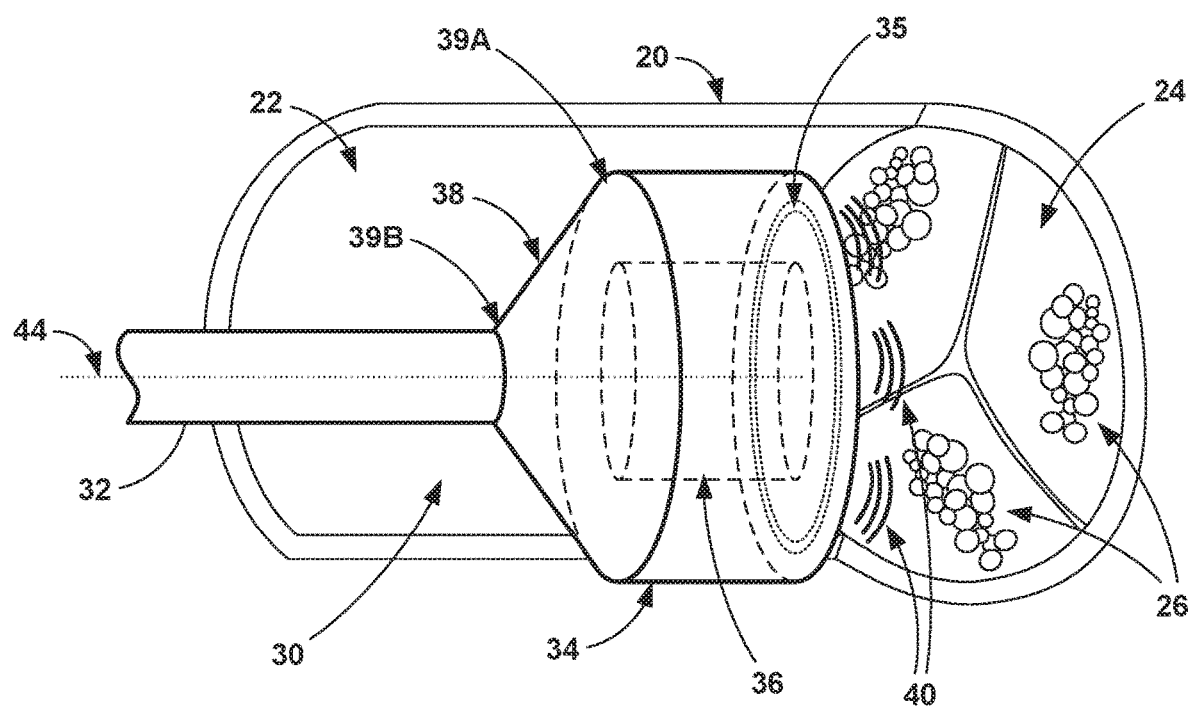
FIG. 3A is a conceptual view of an example medical assembly configured to deliver an electrical signal between electrodes to cause a fluid to undergo cavitation.

FIG. 3A is a conceptual view of an example medical assembly 30 configured to deliver an electrical signal between electrodes 35 to cause a fluid to undergo cavitation. Medical assembly 30 may be similar to medical assembly 12 of FIG. 2A, catheter 32 may be similar to catheter 14 of FIG. 2A, expandable member 34 may be similar to expandable member 16 of FIG. 2A, and filter 38 may be similar to filter 18 of FIG. 2A. As shown in the example of FIG. 3A, which is similar to FIG. 2A, aortic valve 24 includes three leaflets and is disposed upstream from aorta 20. As discussed above, the leaflets of aortic valve 24 may have reduced functionality (e.g., reduced movement of the leaflets), which may be at least partially due to the presence of calcified lesions 26 on each of the leaflets. In order to treat aortic valve 24, medical assembly 30 may be inserted through lumen 22 within aorta 20.

Medical assembly 30 includes expandable member 34 configured to expand from a collapsed configuration (not shown in FIG. 3A) to an expanded configuration as shown in FIG. 3A. This collapsed configuration may enable expandable member 34 and the distal end of medical assembly 30 to navigate the vasculature and/or other narrow spaces in order to reach the target treatment site. Expandable member 34 in the collapsed configuration may be advanced out from catheter 32 to assume the expanded configuration. Expandable member 34 may be expanded until a radially outward surface of expandable member 34 contacts and seals the inner surface of aorta 20 such that all blood and other material passes through channel 36 and towards filter 38. However, in other examples, expandable member 34 may be expanded to a radius smaller than filter 38, and filter 38 seals or approximates the inner surface of aorta 20. Expandable member 34 may also be configured to at least partially define channel 36 through expandable member 34 in the expanded configuration. For example, expandable member 34 may define a torus shape, wherein the radially inward facing surface of the torus defines channel 36. In some examples, expandable member 34 may be a balloon that is inflated with a fluid. For example, catheter 32 may define a lumen or include another inner catheter that is configured as an inflation lumen coupled to expandable member 34 and configured to deliver a fluid to expand expandable member 34. In other examples, expandable member 34 may be an expandable structure formed of an expandable frame, such as an expandable metal frame, which may be covered by a fluid permeable member in some examples.

Medical assembly 30 may also include one or more electrodes 35 carried by expandable member 34. The one or more electrodes 35 are configured to transmit an electrical signal through a fluid (such as the fluid within expandable member 34, although the electrical signal may be transmitted through the blood within lumen 22 of aorta 20 in other examples) to cause the fluid to undergo cavitation that generates a pressure wave within the fluid. Each of the one or more electrodes 35 may receive electrical signals from an energy source external to the patient and via one or more conductors that travel through catheter 32 and expandable member 34. In some examples, one or more electrodes 35 includes a plurality of electrodes carried by expandable member 34. The plurality of electrodes may be configured to transmit the electrical signal between at least two electrodes of the plurality of electrodes. For example, the plurality of electrodes may include at least two concentric ring electrodes. The electrical signal may then travel between the two concentric ring electrodes and generate pressure pulse waves 40 in the blood which travel towards and fracture calcified lesions 26. In some examples, all of the electrodes are carried on or within expandable member 34. In other examples, one or more electrodes 35 may be carried by expandable member 34, and a separate ground electrode (or electrode or other polarity) is inserted through catheter 32 and channel 36, e.g., on a guidewire extending through a lumen of catheter 32 and through channel 36 (not shown in FIG. 3A).

In some examples, one or more electrodes 35 may be disposed at a distal end of expandable member 34. In this manner, one or more electrodes 35 may be configured to generate pressure pulse waves 40 that travel distally away from expandable member 34 and towards calcified lesions 26 on the surface of the leaflets of aortic valve 24. In addition to or instead of the electrodes 35 at the distal end of expandable member 34, in some examples, one or more electrodes 35 may be disposed at a radially outward surface (and at a proximal, middle, or distal axial location of expandable member 34, for example) of expandable member 34 such that one or more electrodes 35 can generate pressure pulse waves that travel radially outward from expandable member 34. Radially outward traveling pressure pulse waves may be configured to treat the leaflets when at least a portion of expandable member 34 is disposed within aortic valve 24. One or more electrodes 35 may be disposed within expandable member 34 and/or coupled to an exterior surface of expandable member 34. In some examples, one or more electrodes 35 are constructed of nitinol, but other materials, such as stainless steel, platinum, alloys, or any combination thereof. A shape memory material such as nitinol may promote expansion of electrodes 35 once removed from a collapsed configuration within catheter 32.

In some examples, pressure pulse waves 40 may fracture portions of calcified lesions 26 from aortic valve 24, resulting in calcified fragments traveling in the bloodstream. Medical assembly 30 may also include filter 38 disposed proximal of expandable member 34 in the expanded configuration. Filter 38 may be sized such that blood constituents (e.g., plasma, red blood cells, white blood cells, platelets, and the like) pass through the pores in filter 38 and most if not all of the fragments of calcified lesion do not pass filter 38. Therefore, fragments of calcified lesion may pass through channel 36 in expandable member 34 and captured by medical assembly 30. In some examples, filter 38 may be formed from a polymer, a metal mesh, or any combination thereof, such as the materials and methods described with respect to filter 18 above.

Filter 38 may be configured to expand from a collapsed filter configuration (not shown in FIG. 3A) when stored within catheter 32 to an expanded filter configuration as shown in FIG. 3A. Filter 38 may define a conical shape in the expanded filter configuration, where the conical shape has a distal filter diameter larger than a proximal filter diameter. However, other shapes for filter 38 are possible and may be determined by one or more portions of expandable member 34 to which filter 38 is attached. The distal end 39A of filter 38 (e.g., the end of filter 38 closer to expandable member 34) may be coupled to the proximal end of expandable member 34, and the proximal end 39B (e.g., the end of filter 38 furthest from expandable member 34) of filter 38 may be coupled to catheter 32 or a structure within catheter 32, for example. In some examples, filter 38 may be constructed of a nitinol mesh or other material that can reside in the collapsed configuration and then be expanded out from catheter 32.

Medical assembly 30 may also include components not shown in FIG. 3A. For example, medical assembly 30 may include a first electrical conductor coupled to a first electrode of the one or more electrodes 35 and a second electrical conductor coupled to a second electrode of the one or more electrodes 35. An energy source may also be configured to generate and deliver the electrical signal between the first electrode and the second electrode of electrodes 35 via the first electrical conductor and the second electrical conductor. In other examples, three or more electrodes may be configured to transmit the electrical signals within the fluid in expandable member 34 and cavitation which generates different types of pressure pulse waves and/or direct pressure pulse waves in different directions within lumen 22 with respect to expandable member 34.

The electrical signal may be delivered through a fluid (such as blood within aorta 20) via two electrodes of electrodes 35 to heat a portion of the fluid to generate a steam/plasma bubbles within the fluid. The steam/plasma bubbles may represent relatively low-pressure pockets of vapor generated from the surrounding fluid. The low-pressure steam/plasma bubbles eventually collapse in on themselves due to the relatively high pressure of the surrounding fluid and heat loss of the steam/plasma bubbles to the surrounding fluid. As the steam/plasma bubbles collapse, the bubbles release a large amount of energy in the form of a high-energy pressure pulse waves 40 within the fluid. In some examples, the formation and subsequent collapse of the steam/plasma bubbles may be short lived or nearly instantaneous, causing the pressure pulse waves 40 to originate near the source of energy delivered to the fluid by electrodes 35.

The electrical signal transmitted may be delivered as a corona, an electrical arc, a spark, or the like between two electrodes of electrodes 35 using the fluid within aorta 20 as the conductive media. In some examples, one electrode of electrodes 35 may represent the return electrode such that the current density along the exposed surface area (e.g., exposed to the fluid) of the return electrode is maximized. Additionally, or alternatively, the exposed surface areas of the current delivery electrode of electrodes 35 may be relatively small to maximize the current density on the exposed surface. In other words, the current delivery electrode or electrodes may be constructed as only a portion of a larger structure on which the electrodes are carried. In some examples, the size or material of any of electrodes 35 may be selected to accommodate the desired current. In some examples, the respective exposed surface of each primary electrode (e.g., the current delivery electrode) may be less than about 0.1 square millimeters ($mm^2$) to provide the surface for the formation of the plasma/steam bubbles to occur.

In some examples, the separation distance between electrodes 35 over which the electrical signal travels may be set depending on the type of electrical signal intended to be transmitted between the electrodes. For example, for arc-type cavitation, the electrodes of opposite polarity may be separated by a distance of about 0.005 inches to about 0.020 inches (e.g., about 0.13 mm to about 0.5 mm). For corona-type cavitation, the electrodes of opposite polarity may be separated by a distance of about 0.005 inches to about 0.050 inches (e.g., about 0.13 mm to about 1.3 mm), or may be separated by even larger distances.

Once formed within the fluid, pressure pulse waves 40 may propagate through the fluid where they impact the afflicted tissue transmitting the mechanical energy of the pressure pulse wave into the tissue and calcified lesions 26. The energy transmitted to calcified lesions 26 may cause the calcium buildup to fracture or break apart allowing target treatment site to be subsequently expanded (e.g., via expandable member 34) to a larger flow diameter.

In some cases, the calcification of calcified lesions 26 may not release into a blood stream of a patient. In other cases, however, at least some calcification may break away from lesions 26 and create emboli that releases into a blood stream of a patient. In some examples, the cavitation procedure may be performed in conjunction with an embolic protection element, e.g., filter 38, positioned downstream of the target treatment site to collect emboli and any portions of calcified lesions 26 that may be dislodged by pressure pulse waves 40. The embolic protection element can be any suitable device, including, but not limited to, a blood permeable membrane or wire mesh mechanically connected to an elongated member. Although filter 38 or an embolic protection element may be shows as coupled to catheter 32, filter 38 or the embolic protection element may be carried by or otherwise attached to a different elongate member in other examples.

In some examples, expandable member 34 may carry a plurality of primary electrodes (e.g., current delivery electrodes), which may be distributed about expandable member 34. The plurality of primary electrodes may be electrically connected together (e.g., in series or parallel) or may be electrically isolated from each other and electrically connected to respective electrical conductors disposed within catheter 32. The plurality of primary electrodes may have any suitable configuration, and can be an integral part of expandable member 34 or may be carried by expandable member 34 and mechanically connected to expandable member 34. In some examples, the plurality of electrodes 35 (e.g., primary electrodes in some examples) may be positioned at distal end of expandable member 34 such that when expandable member 34 is in the expanded configuration, the plurality of primary electrodes are distributed in a ring pattern. One or more return electrodes (e.g., secondary electrodes) may be provided in a concentric ring pattern with the primary electrodes, with a single larger electrode constructed as a ring or disc, or delivered within channel 36 via an elongated member (e.g., a guidewire) that is extendable from within catheter 32.

In some examples, electrodes 35 may be described as including a "primary" or a "secondary" electrode to merely differentiate one set of electrodes from another and is not intended to indicate a preference among the electrodes, limit the direction in which an electrical signal is transmitted from one electrode to another, or designate where the cavitation initiates unless described otherwise in the examples. Further the term "electrode" may refer to the component(s) or portions of the component(s) that are used to induce cavitation within a fluid and is not intended to describe the entire cavitation system.

The fluid may include any fluid capable of undergoing cavitation via energy delivered to the fluid by the electrodes. Generally, the fluid may be fluid within expandable member 34, particularly when electrodes 35 are contained within expandable member 34. In other examples, the fluid may be or include blood flowing within the patient. In addition to or instead of blood, in some examples, the fluid may be or include a fluid introduced into the patient (e.g., through a lumen defined by catheter 32 or another catheter within catheter 32 to avoid another catheter external to catheter 32), such as, but not limited to, biocompatible fluids such as saline, phosphate buffered saline (PBS), or similar solution with a salt content between about 0.9 weight percent (wt. %) and about 5 wt. %; contrast media (e.g., about 25 volume percent (vol. %) to about 75 vol. % contrast media), or the like. Saline or other ionic solutions may more readily undergo cavitation compared to blood, thereby requiring less energy to induce cavitation within the fluid. For example, the higher the salt content of the saline fluid, the higher the conductance will be for the fluid, thereby requiring less energy to increase the temperature of the fluid and induce cavitation. Additionally, the higher the concentration of contrast media, the more viscous the fluid will be leading to a higher dissipation of the cavitation bubbles.

In some examples, the fluid may be heated (e.g., body temperature or about 37° C.) prior to introduction into the patient. Heating the fluid may increase the relative vapor pressure of the fluid and thus require less energy to induce cavitation. In these examples, the fluid may include fluid not found in the patient's body, but, rather, introduced by a clinician. In examples in which the fluid is introduced into the patient's body, the fluid may be introduced to the target treatment site using any suitable technique. In some examples, catheter 32 may define one or more perfusion lumens configured to provide access to the target treatment site and permit the delivery of the fluid, such as saline, into the vessel or heart via one of supply tubes 58 (shown in FIG. 4).

Expandable member 34 may be one or more balloons in some examples, and the one or more balloons may be formed from any suitable material, such as a flexible polymeric material that is configured to form a tight seal with catheter 32 or a different elongated member within catheter 32. In some examples, expandable member 34 may be formed physically separate from catheter 32 and attached to an exterior surface or interior surface of an inner elongated member via co-extrusion, bonding, adhesives, or the like. In other examples, expandable member 34 may be integrally formed with an inner elongated member such that expandable member 34 is embedded or at least partially embedded in the inner elongated member. In other examples, expandable member 34 may be separated from an inner elongated member such that expandable member 34 forms a tight seal with itself.

Expandable member 34 may be constructed using a flexible polymeric material including, for example, nylon 12, polyethylene, polyethylene terephthalate (PET), silicone, polyvinyl chloride, polypropylene, polyurethanes, polyamides, polyesters, latex, natural rubber, synthetic rubber, polyether block amides, or the like. Additionally, or alternatively expandable member 34 may be constructed with an electrically insulative material and/or an electrically conductive material.

In some examples, expandable member 34 may be configured to be deflatable via a vacuum or other stable source to forcibly remove fluid from the balloon, thereby allowing for quicker collapse and/or a lower cross-sectional profile after the cavitation procedure is completed. Additionally, or alternatively, expandable member 34 may include one or more perfusion ports allowing fluid to continuously flow from the expandable member 34 into the vessel or heart of the patient.

Expandable member 34 may have any suitable size or shape. In some examples, expandable member 34 may define a cross sectional diameter of about 10 mm to about 50 mm in the expanded configuration so that expandable member 34 may be deployed in the fully expanded configuration within aortic valve 24 after the cavitation procedure, e.g., to contact and expand aortic valve 24 as part of a valvuloplasty procedure. Expandable member 34 may also have any suitable length (e.g., measured along longitudinal axis 44). For some procedures used to treat calcifications in or near a heart valve (e.g., aortic valve 24) of a patient, expandable member 34 may define a length of about 15 mm to about 80 mm.

In some examples, catheter 32 may define or include multiple lumens. For example, catheter 32 may define a first lumen within which filter 38 and/or expandable member 34 may reside in the collapsed configurations and a second lumen configured to deliver contrast agent through the second lumen and channel 36 of expandable member 34 in the expanded configuration. In this manner, medical assembly 30 may be configured to deliver contrast agent into the blood stream without another catheter. Imaging of the vasculature (e.g., via computed tomography, magnetic resonance imaging, or fluoroscopy) with contrast agent may aid the clinician in directing pressure pulse waves 40 to target tissue sites having calcified lesions 26, positioning expandable member 34 within the valve to perform the valvuloplasty, and/or deliver a stent to the valve, for example.

Figure 3B:
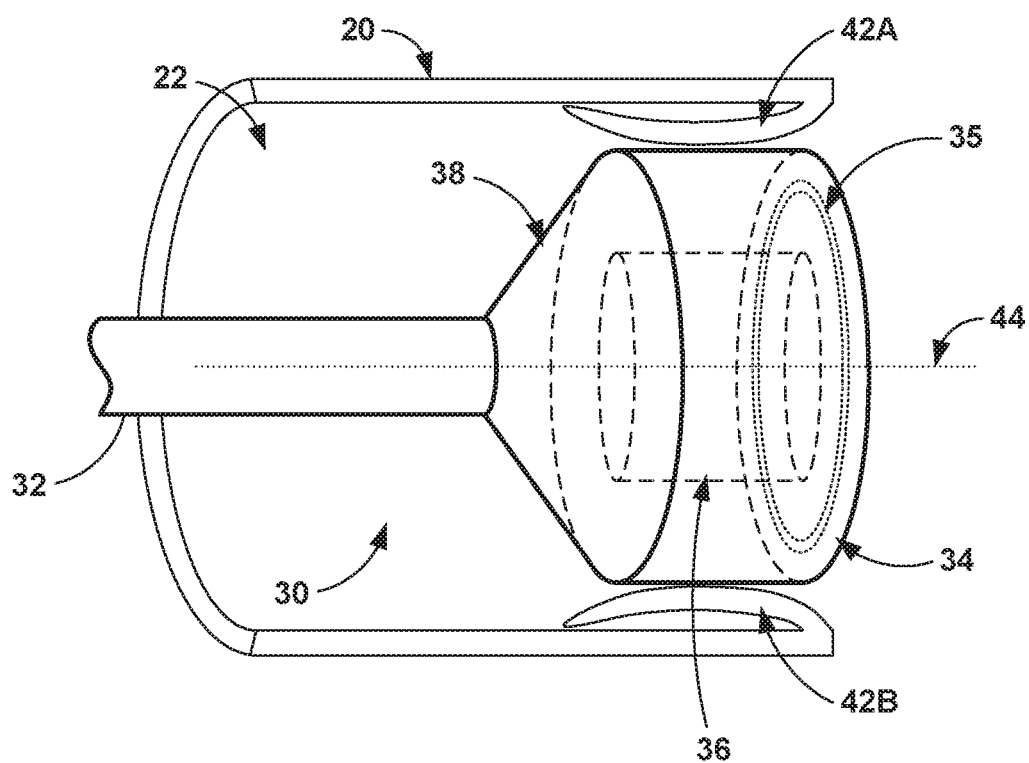
FIG. 3B is a conceptual view of the example medical assembly of FIG. 3A configured to apply a force to leaflets of a heart valve and increase a size of the opening of the heart valve.

FIG. 3B is a conceptual view of the example medical assembly 30 of FIG. 3A configured to apply a force to leaflets 42A and 42B (collectively "leaflets 42) of heart valve 24 and increase the size of the opening of the heart valve 24. As shown in FIG. 3B, expandable member 34 may be used to physically increase the size of the opening of a heart valve (e.g., aortic valve 24) after delivering pressure pulse waves that disrupt calcified lesions 26 on leaflets 42 and may thereby increase the pliability of leaflets 42. After delivering the pressure pulse waves and removing the fractured calcification (if any), expandable member 34 may be reduced in size towards longitudinal axis 44 and the collapsed configuration. For example, expandable member 34 may be collapsed to be withdrawn back within catheter 32. However, expandable member 34 may or may not need to be fully collapsed and retracted into catheter 32.

Once expandable member 34 is at least partially collapsed (not shown in FIG. 3B), expandable member 34 may be advanced to a position at least partially within heart valve 24. Once positioned within the heart valve, expandable member 34 may again be expanded into the expanded configuration. This expansion produces a radial force away from longitudinal axis 44 and against the surface of leaflets 42. As expandable member 34 continues to expand, expandable member 34 forces leaflets 42 towards the outer edge of heart valve 24 to increase the size of the opening of heart valve 24 and increase blood flow. This portion of the procedure may be referred to as a valvuloplasty. During this procedure, blood may continue to pass through channel 36 and filter 38. After the valvuloplasty, in some examples, a clinician may insert a heart valve prosthesis through a lumen in catheter 32 and channel 36 and into the native valve 24. Once these procedures are complete, expandable member 34 and filter 38 may be collapsed and retracted within catheter 32 for removal from the patient via the artery insertion location.

Figure 4:
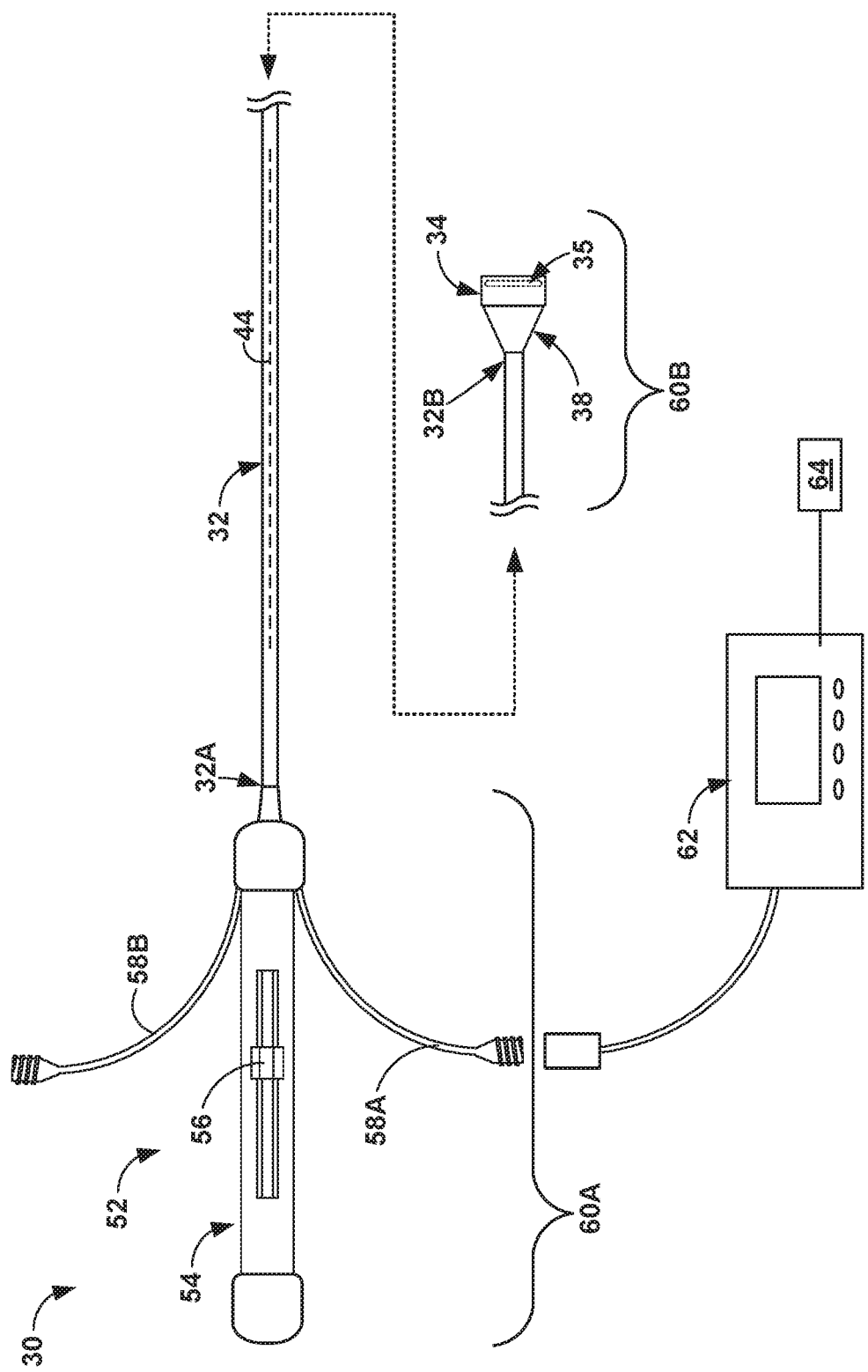
FIG. 4 is a conceptual view of an example medical assembly that includes a catheter including the expandable member of FIGS. 2 and 3.

FIG. 4 is a conceptual view of an example medical assembly 30 that includes a hub portion 54, a catheter 32, and expandable member 34 of FIGS. 2 and 3. Medical assembly 30 also includes energy source 62 configured to generate and deliver an electrical signal between electrodes, such as electrodes 35, through a fluid in contact with the electrodes and/or expandable member 34 to cause the fluid to undergo cavitation to generate a pressure pulse wave within the fluid. In some examples, at least one of the electrodes via which assembly 30 delivers an electrical signal may be physically separate from expandable member 34 and may be attached to a separate device (e.g., a guidewire) that is delivered via a lumen within catheter 32 and channel 36 defined by expandable member 34.

Expandable member 34 and one or more electrodes 35 (e.g., which may include one or more primary electrodes and/or one or more secondary electrodes) may have any suitable configuration. In some examples, one or more electrodes 35 may be an integral part of expandable member 34. In other examples, one or more electrodes 35 may be separate from and mechanically connected to expandable member 34. In either case, one or more electrodes 35 may be described as being carried by expandable member 34. In some examples, one or more electrodes 35 may be physical structures configured as electrodes or to include one or more electrically conductive portions. In other examples, expandable member 34 may include one or more electrically conductive materials as part of the expandable member 34 to act as at least one, or all, of one or more electrodes 35.

Expandable member 34 is configured to expand from a collapsed configuration to an expanded configuration at a target treatment site within cardiovasculature of a patient. In some examples, expandable member 34 may be configured to self-expand from the collapsed configuration to the expanded configuration. For example, expandable member 34 may include an expandable frame composed of a shape memory or super-elastic material such as nickel-titanium (e.g., Nitinol) configured to self-expand to the expanded configuration when expandable member 34 is unconstrained. In other examples, expandable member 34 may be a balloon or other sealed structure in which a fluid is delivered into the balloon to change expandable member 34 from the collapsed configuration to the expanded configuration. The fluid may be delivered to expandable member 34 via an inflation lumen within catheter 32, and in fluid communication with a fluid source.

As shown in FIG. 4, expandable member 34 may be mechanically connected to, or connected to a structure within, a catheter 32 configured to deliver expandable member 34 to target treatment site within the heart or vasculature of the patient. Medical assembly 30 may include catheter 32 extending from proximal end 32A to distal end 32B. The side views of medical assembly 30 shown in FIGS. 5A and 6A illustrates medical assembly 30 along a longitudinal axis 44 of catheter 32. FIGS. 5A and 6A are cross-sectional side views of the distal portion of medical assembly 30 providing greater detail of some of the aspects of medical assembly 30, the cross-section being taken in a direction parallel to longitudinal axis 44. FIG. 5A shows expandable member 34 positioned in a fully collapsed configuration within catheter 32 of medical assembly 30 and FIG. 6A shows expandable member 34 positioned in an expanded configuration, which are described in further detail below. As described further below, one of more electrodes 35 of expandable member 34 may be electrically coupled to energy source 62 via medical assembly 30 while in the fully collapsed and partially expanded configurations.

Medical assembly 30 may include a hub portion 54 connected to proximal end 32A of catheter 32. Hub portion 54, including proximal end 32A of catheter 32, forms part of a proximal portion 60A of medical assembly 30. Medical assembly 30 also includes a distal portion 60B that includes distal end 32B of catheter 32. The designations of proximal and distal portion 60A and 60B are used to describe different regions of medical assembly 30 (as divided along a length of medical assembly 30) and may be of any suitable length. In some examples, catheter 32 may also be characterized as having one or more intermediate portions separating the proximal and distal portions 60A and 60B.

In some examples, catheter 32 may be described as an elongated member and may include one or more additional elongated members within catheter 32. These additional elongated members may be configured to deliver a fluid and/or move relative to catheter 32. These additional elongated members may be co-axial to catheter 32 and/or define completely separate lumens. For example, control member 56 may be coupled to catheter 32 and/or an elongated member within catheter 32. In one example, control member 56 may be coupled to an elongated member to which expandable member 34 is attached such that movement of control member 56 towards catheter 32 and with respect to hub portion 54 may cause the elongated member to push expandable member 34 out of the lumen of catheter 32 and beyond the distal end of catheter 32 to expand from the collapsed configuration into the expanded configuration. Alternatively, control member 56 may be coupled to catheter 32, with expandable member 34 coupled to an elongated member within catheter 32, such that movement of control member 56 in the proximal direction with respect to hub portion 54 may cause the catheter 32 to withdraw proximally from expandable member 34 and the elongated member within catheter 32 to which expandable member 34 is connected. In this manner, retraction of catheter 32 may expose expandable member 34 to enable expansion from the collapsed configuration into the expanded configuration.

Proximal end 32A of catheter 32 may be received within hub portion 54 and can be mechanically connected to hub portion 54 by any suitable technique. Hub portion 54 may include one or more supply tubes 58A and 58B (collectively "supply tubes 58"). Supply tubes 58 may provide access to the various components of distal portion 60B of catheter 32 and may be used for accessing or transporting various items through catheter 32 including, for example, a guidewire (not shown), a fluid for use during the cavitation procedure, one or more electrical conductors 70A and 70B (collectively "electrical conductors 70" shown in FIG. 5A), a fluid for inflating or deflating expandable member 34, or the like. For example, one or more of the supply tubes (e.g., supply tube 58A) may be used to electrically couple one or more electrodes 35 to energy source 62 via electrical conductors 70. Additionally, or alternatively, one or more of supply tubes 58 may be used to perfuse or aspirate portions of the vessel or heart at a target treatment site, used to introduce a guidewire into a guidewire lumen within catheter 32 (not shown in FIG. 4), or the like. For example, one of supply tubes 58 may be used to remove fractured calcifications removed from the heart valve. Although two supply tubes 58 are shown, one supply tube or three or more supply tubes may be shown in other examples. In some examples, each supply tube may be in fluid communication with a respective elongated member defining a lumen or a structure (e.g., an electrical conductor) within catheter 32.

In some examples, medical assembly 30 may include a strain relief body, which may be a part of hub portion 54 or may be separate from hub portion 54. The strain relief body may extend distally from hub portion 54 and may help reduce mechanical strain between hub portion 54 and elongate member 32. Additionally, or alternatively, proximal portion 60A of medical assembly 30 can include another structure in addition or instead of hub portion 54. For example, catheter hub portion 54 may include one or more luers or other mechanisms for establishing mechanical connections, fluidic connections, or other types of connections between medical assembly 30 and other devices.

Hub portion 54 may include a control member 56 configured to actuate the movement (e.g., retraction and advancement) of catheter 32 and/or a different elongated member within catheter 32, such as to expose expandable member 34 and allow expandable member 34 to assume the expanded configuration. Control member 56 may have any suitable design including, for example, a slider, a lever, or a thumbwheel mechanism that when actuated causes the proximal advancement or retraction of either catheter 32 or an inner elongated member relative to the other. For example, control member 56 may be in the form a slider where moving the slider towards distal end 32B, causes catheter 32 to slide proximal relative to the distal end 32B. Control member 56 may include one or more deployment markers that indicate when catheter 32 or an inner elongated member are aligned to permit full expansion of expandable member 34 or full collapse of expandable member 34 within catheter 32.

In some examples, catheter 32 of medical assembly 30 may be used to access relatively distal treatment locations in a patient or other relatively distal tissue sites (e.g., relative to the access point for medical assembly 30). Example treatment locations may include, for example, locations at or near the heart or a heart valve (e.g., aortic valve, mitral valve, or the like) or within the blood vessels of a patient. In some examples, catheter 32 is structurally configured to be relatively flexible, pushable, and relatively kink- and buckle-resistant, so that it may resist buckling when a pushing force is applied to a relatively proximal portion of medical assembly 30 to advance catheter 32 distally through vasculature, and/or so that it may resist kinking when traversing around a tight turn in the vasculature. Unwanted kinking and/or buckling of catheter 32 may hinder a clinician's efforts to push the catheter body distally, e.g., past a turn in the vasculature.

Catheter 32 has a suitable length for accessing a target treatment site within the patient from the vasculature access point. The length may be measured along the longitudinal axis of catheter 32. The working length of catheter 32 may depend on the location of the lesion within the patient's body. For example, if medical assembly 30 is a catheter used to access a target treatment site at or adjacent a heart valve from a femoral access point, catheter 32 may have a working length of about 100 centimeters (cm) to about 200 cm, such as about 110 cm, although other lengths may be used. In other examples, or for other applications, the working length of catheter 32 may have different lengths.

The outer diameter of catheter 32 may be of any suitable size or dimension including, for example, between about 2 millimeter (mm) and about 8 mm. In one example, the outer diameter of catheter 32 may be approximately 8 French (approximately 2.67 mm). In some examples, the outer diameter may be substantially constant (e.g., uniform outer diameter), tapered (e.g. tapered or step change to define a narrower distal portion), or combinations thereof.

In some examples, at least a portion of an outer surface of catheter 32 may include one or more coatings, such as, but not limited to, an anti-thrombogenic coating, which may help reduce the formation of thrombi in vitro, an anti-microbial coating, and/or a lubricating coating. In some examples, the entire working length of catheter 32 is coated with the hydrophilic coating. In other examples, only a portion of the working length of catheter 32, e.g., including distal portion 60B, may be coated with the hydrophilic coating. This may provide a length of catheter 32 distal to hub portion 54 that does not include a hydrophilic coating and with which the clinician may grip catheter 32, e.g., to rotate catheter 32 or push catheter 32 through vasculature. In some examples, the entire working length of catheter 32 or portions thereof may include a lubricious outer surface, e.g., a lubricious coating. The lubricating coating may be configured to reduce static friction and/or kinetic friction between catheter 32 and tissue of the patient as catheter 32 is advanced through the vasculature.

In some examples, catheter 32 may also include one or more radiopaque markers which may help a clinician determine the positioning of catheter 32 relative to a target treatment site. For example, one or more radiopaque markers may be positioned proximal, within, or distal to the housing area for expandable member 34, adjacent to filter 38, or combinations thereof. In some examples, portions of expandable member 34, electrodes 35, and/or filter 38 themselves may be radiopaque.

FIG. 5A is a cross-sectional view of the distal portion 32B of catheter 32 of FIG. 4 when expandable member 34 is in the collapsed configuration. As shown in the example of FIG. 5A, in some examples, the distal portion 32B of catheter 32 is also the distal end 60B of medical assembly 30 when expandable member 34 is collapsed (unexpanded) and contained within lumen 82 of catheter 32. Catheter 32 defines an outer elongated member, or outer sheath, that may be configured to maintain elongated member 34 in the collapsed, relatively low-profile configuration in order to deliver expandable member 34 to the target treatment site within the vasculature of the patient.

In the example shown in FIG. 5A, assembly 30 includes elongated member 71, which provides a support structure that attaches to filter 38 and/or expandable member 34. Movement of elongated member 71 relative to catheter 32 may cause filter 38 and expandable member 34 to be exposed from, or retracted within, catheter 32. In some examples, elongated member 71 may be mechanically coupled to a proximal end of filter 38 in the collapsed configuration, and the distal end of filter 38 may be coupled to the proximal end of expandable member 34. In other examples, at least a portion of elongated member 71 may structurally attach to a portion of expandable member 34 to provide support to expandable member 34 the collapsed and/or expanded configuration. Elongated member 71 may define respective channels through which electrical conductors 70A and 70B travel to provide electrical conductivity between an energy source (e.g., energy source 62) and respective electrical contacts 72A and 72B. Electrical contacts 72A and 72B may be electrically coupled (e.g., physically coupled) to electrical conductors 74A and 74B, respectively, which travel passed and/or through at least a portion of filter 38 and expandable member 34. Each of electrical conductors 74A and 74B may terminate at respective electrodes 76 and 78.

Electrical conductors 70A, 70B, 74A, and/or 74B may have any suitable configuration. In some examples, the wires forming any electrical conductors may be braided, coiled, or linearly extended along the longitudinal length of catheter 32. Additionally, or alternatively, electrical conductors 70 may contribute or form part of the support structure (e.g., a coil and/or a braid) of elongated member 71 or other structure. Electrical conductors 70 and 74 may be electrically insulated from one another by an electrically insulating sheath or by the body of elongated member 71 which may be comprised of electrically non-conductive material (e.g., fluorinated ethylene propylene (FEP)).

Inner elongated member 80 may reside radially within filter 38 and expandable member 34 in the collapsed configuration. Inner elongated member 80 may define lumen 82, through which one or more fluids or structures may be delivered out of the distal end of catheter 32. For example, inner elongated member 80 may enable a guidewire or contrast agent to be delivered out of catheter 32. A guidewire may be used to help navigate distal portion 60B to a target treatment site. For example, the guidewire may be introduced through vasculature of a patient to a target treatment site and distal portion 60B of medical assembly 30 may be advanced over the guidewire to navigate catheter 32 through the vasculature of the patient to the target treatment site. Contrast agent may be used to image the vasculature prior to or during a medical procedure. In other examples, inner elongated member 80 may be configured to enable passage of a heart valve prosthesis (e.g., a stent) that may be delivered to the heart valve through the channel in the expandable member 34 when in the expanded configuration. In some examples, elongated member 71, filter 38, and expandable member 34 may be configured to move longitudinally with respect to inner elongated member 80.

In the collapsed configurations, filter 38 and expandable member 34 may reside within the space defined between catheter 32 and inner elongated member 80. Filter 38 may, in some examples, be folded in a circumferential and/or longitudinal direction in the collapsed configuration. In examples in which filter 38 is folded in a longitudinal direction, filter 38 may obtain a larger dimension in the longitudinal direction, in addition to the radial direction, when expanded to the expanded configuration. Similarly, expandable member 34 may be folded in a circumferential and/or longitudinal direction in the collapsed configuration. These folds or curves may be present when expandable member 34 is a rigid material or a flexible material. In addition, in some examples in which expandable member 34 is a balloon, the material of expandable member 34 may contract in the collapsed configuration and stretch in the expanded configuration, although some folding may also occur even with stretchable materials. Although gaps between filter 38 and expandable member 34 and catheter 32 and/or inner elongated member 80 may be shown in FIG. 5A, at least a portion of filter 38 and/or expandable member 34 may be in contact with catheter 32 and/or inner elongated member 80 in other examples.

When expandable member 34 is in the collapsed configuration, electrodes 76 and 78 carried by expandable member 34 may also be collapsed or otherwise fit within the space between catheter 32 and inner elongated member 80. If electrodes 76 and 78 are constructed in the shape of respective rings, then each ring may be flexible and bend into a collapsed configuration. In some examples, electrodes 76 and 78 may include one or more channels, holes, skives, ramps, or other structures that facilitate collapse of electrodes 76 and 78 into a particular, or predetermined, shape. As used herein "carried by" or "carried along" is used to describe electrode configurations in which the electrode is attached, connected, or adhered directly or indirectly to part of expandable member 34 or extends within or is embedded within expandable member 34. In some examples, one or more other electrodes, such as a ground electrode, may be extended through lumen 82 or carried as a part of inner elongated member 80, for example.

FIGS. 5B, 5C, and 5D are cross-sectional views of different axial positions along catheter 32 of FIG. 5A. FIG. 5B corresponds to the cross-section at location A in FIG. 5A, FIG. 5C corresponds to the cross-section at location B in FIG. 5A, and FIG. 5D corresponds to the cross-section at location C in FIG. 5A. As shown in FIG. 5B, elongated member 71 is positioned within a lumen defined by catheter 32. Electrical conductors 70A and 70B are disposed at different circumferential locations within elongated member 71. In addition, inflation lumen 73 may be defined by elongated member 71. Inflation lumen 73 may facilitate the transfer of a fluid to and from expandable member 34, where the fluid may be provided by an external fluid source coupled to a proximal end of inflation lumen 73. In other examples, inflation lumen 73 may be defined by a separate elongated member, a space between elongated member 71 and inner elongated member 80. Inner elongated member 80 may be disposed within a lumen defined by elongated member 71. Although catheter 32, elongated member 71, and inner elongated member 80 may be concentric, or share a common central axis, as shown, but other configurations are also contemplated.

As shown in FIG. 5C, filter 38 in the collapsed configuration is positioned within the lumen defined by catheter 32. Electrical conductors 74A and 74B are disposed at different circumferential locations within the collapsed filter 38, which may be within or outside of boundaries defined by filter 38. In addition, inflation lumen 73 may be defined by a dedicated elongated member separate from, but may be attached to, elongated member 71. In other examples, elongated member 71 and filter 38 may define different portions of inflation lumen 73. Inner elongated member 80 may be disposed radially inward of filter 38 in the collapsed configuration.

As shown in FIG. 5D, expandable member 34 in the collapsed configuration is positioned within the lumen defined by catheter 32. Electrical conductors 74A and 74B are disposed at different circumferential locations within expandable member 34. Electrical conductors 74A and 74B may disposed outside of expandable member 34 in other examples. Inner elongated member 80 may be disposed radially inward of expandable member 34 in the collapsed configuration.

FIG. 6A is a cross-sectional view of the distal end of catheter 32 of FIG. 4 when expandable member 34 is in the expanded configuration. As shown in the example of FIG. 6A, the distal end 60B of medical assembly 30 is the distal end of expandable member 34. However, elongated member 71 has been translated longitudinally with respect to catheter 32 (e.g., by moving member 71 distally, moving catheter 32 proximally, or any combination thereof) and inner elongated member 80 to expose filter 38 and expandable member 34 to enable filter 38 and expandable member 34 to transition from the collapsed configuration to the expanded configuration.

In the expanded configuration, filter 38 may assume a conical shape defined by inner wall 90B and outer wall 90A. Inner wall 90B may be coupled to a distal end of elongated member 71 and a proximal end of expandable member 34 near a radially inner surface 92B of expandable member 34. Outer wall 90A may be coupled to a distal end of elongated member 71 and a proximal end of expandable member 34 near a radially outer surface 92A of expandable member 34. Filter 38 may be attached to expandable member 34 by an adhesive, welding, molding, or other technique. Although filter 38 is shown having two walls in the example of FIG. 6A, filter 38 may have a single wall in some examples or additional walls in other examples. A single wall may be disposed in the place of outer wall 90A or inner wall 90B. In other examples, a single wall may have a thickness that, when expanded, approximates the thickness of expandable member 34 in the expanded configuration. Electrical conductors 74A and 74B may travel between inner wall 90B and outer wall 90A, but electrical conductors 74A and 74B may be disposed outside of filter 38 (e.g., radially inward or radially outward of filter 38) in other examples.

In some examples, filter 38 may be constructed of a nitinol mesh or a mesh of another material. For example, filter 38 may be alternatively, or additionally, constructed of a fabric or polymer. In some examples, filter 38 may be self-expanding or expanded via the expansion of expandable member 34. The mesh of filter 38 may define pores larger than blood constituents and smaller than most, if not all, of calcified fragments dislodged by the created pressure pulse waves. In general, since expandable member 34 may partially or fully seal against the wall of the artery, calcified fragments may be directed with blood flow through channel 100 defined by expandable member 34 and into filter 38. Channel 100 is an example of channel 36 in FIGS. 2 and 3. Calcified fragments and/or emboli may be captured by filter 38 while blood constituents may continue to pass through filter 38 and into the rest of the vasculature. In other examples, filter 38 may be separate from expandable member 34 and supported by another structure, such as catheter 32 or another structure proximal from expandable member 34.

In the expanded configuration, expandable member 34 may define radially outer surface 92A and radially inner surface 92B of a torus shape. The outer diameter of expandable member 34 may be between approximately 5 mm and 50 mm in some examples. In some examples, the inner diameter that defines the channel within inner surface 92B may be approximately equal to the outer diameter of catheter 32. In some examples, the outer diameter and inner diameter of expandable member 34 may be limited in the expanded configuration based on the size of the vessel or valve to be treated.

In some examples, in the expanded configuration, electrodes 76 and 78 may be arranged as concentric rings. In some examples, the entire surface of each concentric ring may be electrically conductive. In other examples, only a portion, or portions, or one or both of the concentric rings may be electrically conductive. For example, an electrically insulative layer may cover portions of the concentric rings with the exception of surfaces which are constructed to transmit an electrical signal. For example, each concentric ring may provide one, two, three, four, five, six, or more electrically conductive portions equidistant or at varied distances around the circumference of the ring.

FIGS. 6B, 6C, and 6D are cross-sectional views of different axial positions along the medical assembly 30 of FIG. 6A. FIG. 6B corresponds to the cross-section at location D in FIG. 6A, FIG. 6C corresponds to the cross-section at location E in FIG. 6A, and FIG. 6D corresponds to the cross-section at location F in FIG. 6A. As shown in FIG. 6B, elongated member 71 is positioned within a lumen defined by catheter 32. Electrical conductors 70A and 70B are disposed at different circumferential locations within elongated member 71. In addition, inflation lumen 73 may be defined by elongated member 71.

As shown in FIG. 6C, filter 38 is in the expanded configuration, with outer wall 90A radially outward of inner wall 90B to define filter space 97. Inner wall 90B defines filter channel 96, which is the channel in which blood of a patient may flow when assembly 30 is positioned within cardiovasculature of the patient. Electrical conductors 74A and 74B and inflation lumen defined by a dedicated elongated member are disposed at different circumferential locations in between outer wall 90A and inner wall 90B.

As shown in the example of FIG. 6D, expandable member 34 in the expanded configuration, with outer surface 92A and inner surface 92B defining expanded space 94, which is a torus shape. Electrical conductors 74A and 74B are disposed at different circumferential locations within expandable member 34. Inner surface 92B defines channel 100. In some examples, a ground electrode (e.g., secondary electrode), contrast agent, or heart valve prosthesis may be delivered through channel 100.

Figure 7:
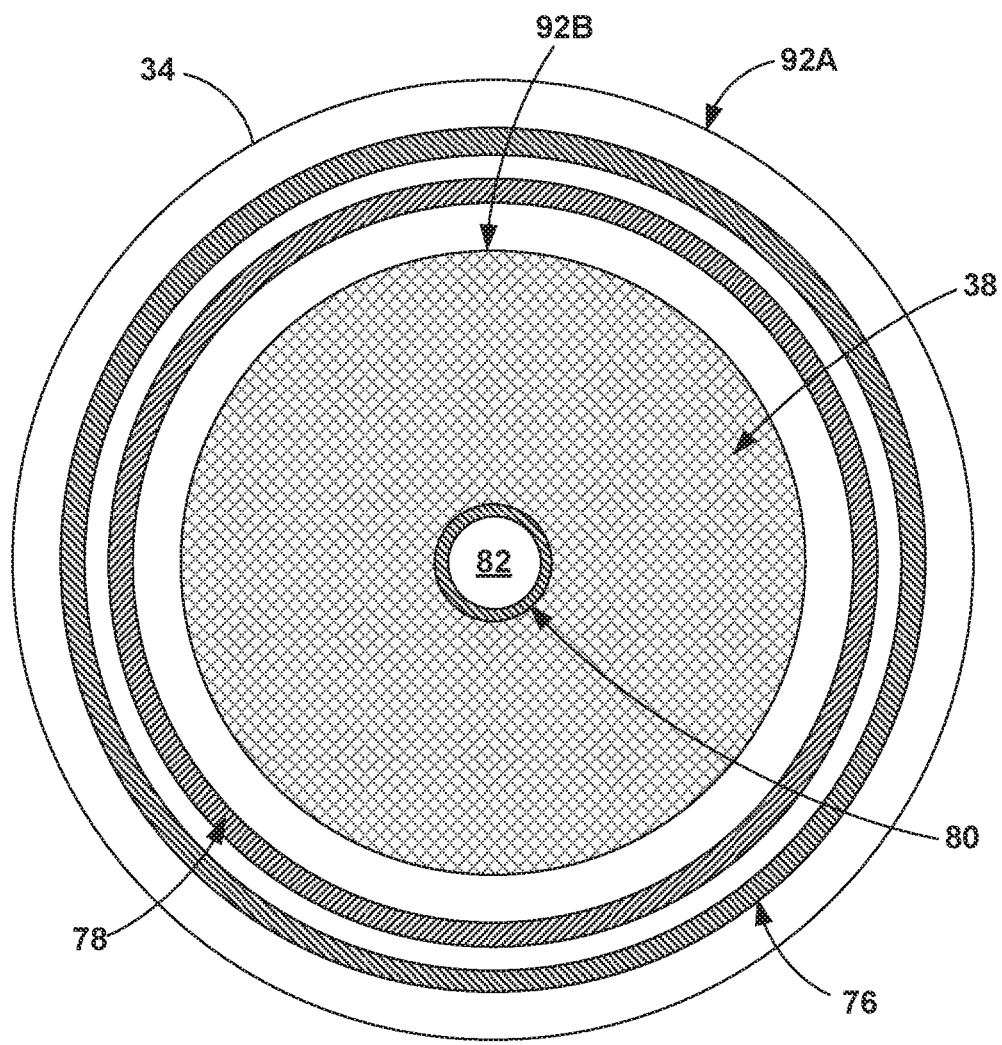
FIG. 7 is a conceptual view of a distal end of an example expandable member carrying a plurality of concentric electrodes.

FIG. 7 is a conceptual view of a distal end of expandable member 34 carrying a plurality of concentric electrodes 76 and 78. Concentric electrodes 76 and 78 are shaped as rings, with electrode 78 having a smaller diameter than electrode 76. This concentric configuration may provide one or more advantages, such as generating cavitation all around the distal surface of expandable member 34 towards the target structure. In some examples, the entirety of one or more of electrodes 76 and 78 are electrically conductive and configured to be exposed to fluid, such that the entirety of electrodes 76, 78 may be configured to transmit an electrical signal. In other examples, only a portion of one or both electrodes 76 and 78 may be configured to be exposed to fluid, such that the electrical signal may be transmitted at discrete portions of electrodes 76, 78. For example, portions of concentric electrodes 76 and 78 may be covered by an electrically insulative material (e.g., a polymer or other type of material) and other portions of concentric electrodes 76 and 78 may be exposed. The exposed portions may be in various shapes, such as circles, ovals, squares, pentagons, strips, amorphous shapes, and/or any other type of shapes. In this manner, electrical current may be transmitted between the exposed portion(s) of concentric electrode 76 and the exposed portion(s) of concentric electrode 78 when electrodes 76 and 78 have opposite polarity.

In some examples, concentric electrodes 76 and 78 may have the same diameter and positioned coaxially at different axial positions. In other examples, concentric electrodes 76 and 78 may have different diameters and disposed at the same axial position such that one of the rings is nested within the larger ring. In still other examples, concentric electrodes 76 and 78 may have different diameters and disposed ad different axial positions (e.g., not overlapping or only partially overlapping). In any case, each ring electrode 76 and 78 may be completely exposed. In other examples, electrodes 76 and 78 may be covered by an insulator and one or more portions of the insulation on each electrode may be removed or otherwise not provided in order to expose specific areas of each electrode. For example, insulation may be removed from portions of electrodes 76 and 78 that face each other (e.g., axially facing surfaces for electrodes at different axial positions or radially facing surfaces for nested electrodes at the same axial position). Therefore, electrical current will only flow between the exposed portions of electrodes 76 and 78.

In other examples, concentric electrodes 76 and 78 may have the same diameter and stacked. In this stacked configuration, electrodes 76 and 78 may be covered by an electrically insulative material and also separated by an electrically insulative material (e.g., instead of fluid or other cavity between each electrode). One or more holes (or one or more cavities of any shape) may be drilled or formed through at least one of electrodes 76 and 78 and the insulation such that the holes allow an electrical signal to pass between the exposed portions of electrodes 76 and 78. In some examples, a plurality of holes, such as three, four, five, or more holes, may be formed to allow electrical signals to pass between electrodes 76 and 78 at these locations. The holes may be in an axially facing direction to direct cavitation towards the distal end of the device. In some examples, additional insulation may be removed from the portion of the electrode around each hole to facilitate the electrical signal propagation and cavitation of surrounding material. In other examples, concentric electrode 76 may have a smaller diameter than electrode 78 and nested within electrode 78 such that electrodes 76 and 78 are only separated by insulation at radial surfaces of each electrode. The one or more holes may, in this example, be formed from the outer radial surface and through portions of the insulation in order to allow electrical signals to pass between electrodes 76 and 78. In this manner, the radially formed holes may enable cavitation to propagate radially outward from the concentric electrodes 76 and 78 and the device. Any of these examples may be used separately or in combination with other examples.

In some examples, concentric electrodes 76 and 78 may be carried on a distal external surface of expandable member 34. In other examples, concentric electrodes 76 and 78 may be disposed within expandable member 34. Even if concentric electrodes 76 and 78 are disposed within expandable member 34, the electrical signal transmitted between the electrodes may cause cavitation and the production of pressure pulse waves described herein. The size and position of each electrode 76 and 78, and the distance of each electrode from the surface of expandable member 34, may be selected to generate desired pressure pulse waves.

In some examples, each of concentric electrodes 76 and 78 may have respective electrical conductors 74A and 74B that separately run through expandable member 36 and conduct electrical signals to and from each electrode. In other examples, a single cable with two electrical conductors may be disposed within expandable member 36 such that one conductor contacts electrode 76 and another conductor contacts electrode 78. In some examples, one electrical conductor may contact electrode 76 or 78, while the other electrical conductor passes through and exiting the electrode before reach the other electrode. For example, one of the electrical conductors of the cable may be electrically coupled to electrode 76 and the other electrical conductor of the cable may then be insulated as it traversed from electrode 76 to electrode 78. In some examples, the insulated electrical conductor may travel through a hole or channel in electrode 76 before electrically coupling with electrode 78.

In other examples, instead of concentric electrodes 76 and 78, one or more separate electrodes may be disposed at different locations within or outside of expandable member 34. Separate electrodes may be formed in 3D shapes such as cylinders, spheres, cubes, or other shapes, or structures with only exposed flat or curved surfaces in various shapes. These different electrodes may all be used to generate cavitation within the fluid or one or more electrodes may be selected to generate cavitation at selected portions of expandable member 34. In this manner, any of electrodes carried by expandable member 34 may be disposed at any location to generate cavitation and pressure wave in any direction (e.g., axially and/or radially) from expandable member 34.

Figure 8:
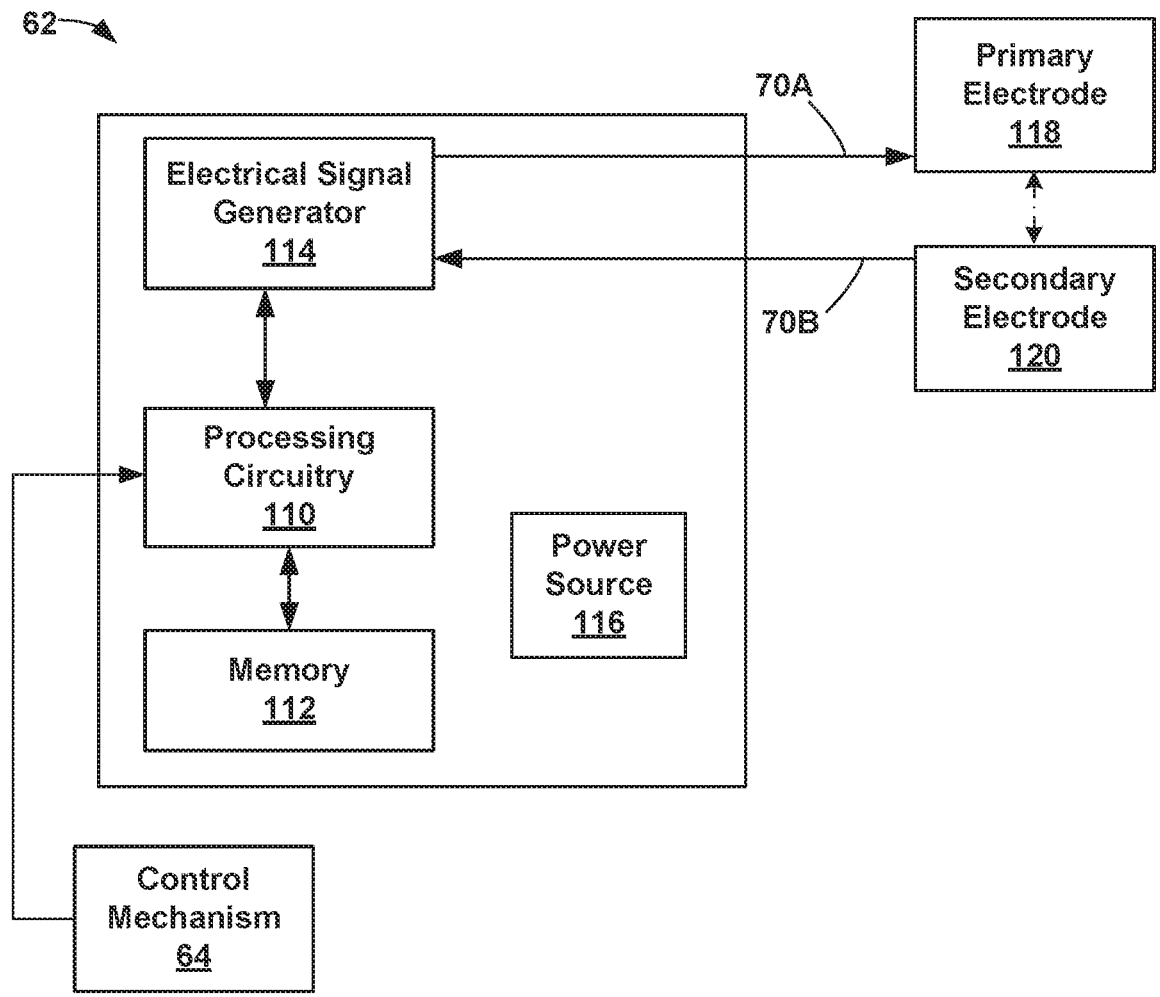
FIG. 8 is a block diagram of an example energy source that may be used with or part of the medical assemblies described herein to induce cavitation within a fluid.

FIG. 8 is a block diagram of an example energy source 62 that may be used with or part of the medical assemblies described herein to induce cavitation within a fluid. As shown in FIG. 8, energy source 62 includes control mechanism 64, processing circuitry 110, memory 112, electrical signal generator 114, and power source 116.

Processing circuitry 110 may include any one or more microprocessors, controllers, digital signal processors (DSPs), application specific integrated circuits (ASICs), field-programmable gate arrays (FPGAs), discrete logic circuitry, or any processing circuitry configured to perform the features attributed to processing circuitry 110. The functions attributed to processors described herein, including processing circuitry 110, may be provided by a hardware device and embodied as software, firmware, hardware, or any combination thereof. In some examples, processing circuitry 110 may include instructions to recognize a particular electrode configuration or allow a clinician to manually input the specific electrode configuration. In some examples, energy source 62 may include additional components such as, a display device or user input device that are not expressly shown for displaying information from processing circuitry 110 or allowing the clinician to input information. In other examples, energy source 62 may additionally, or alternatively, control expansion or contraction of expandable member 34 by delivering fluid to expandable member 34 and/or removing fluid from expandable member 34.

Memory 112 may include any volatile or non-volatile media, such as a random access memory (RAM), read only memory (ROM), non-volatile RAM (NVRAM), electrically erasable programmable ROM (EEPROM), flash memory, and the like. Memory 112 may store computer-readable instructions that, when executed by processing circuitry 110, cause processing circuitry 110 to perform various functions described herein. Memory 112 may be considered, in some examples, a non-transitory computer-readable storage medium including instructions that cause one or more processors, such as, e.g., processing circuitry 110, to implement one or more of the example techniques described in this disclosure. The term "non-transitory" may indicate that the storage medium is not embodied in a carrier wave or a propagated signal. However, the term "non-transitory" should not be interpreted to mean that memory 112 is non-movable. As one example, memory 112 may be removed from energy source 62, and moved to another device. In certain examples, a non-transitory storage medium may store data that can, over time, change (e.g., in RAM).

Processing circuitry 110 is configured to control energy source 62 and electrical signal generator 114 to generate and deliver the electrical signal between primary and secondary electrodes 118 and 120 (e.g., some or all of electrodes 35 or electrodes 76 and 78) to induce cavitation of a fluid. Electrical signal generator 114 includes electrical signal generation circuitry and is configured to generate and deliver an electrical signal in the form of pulses and/or a continuous wave electrical signal. In the case of electrical pulses, electrical signal generator 114 may be configured to generate and deliver pulses having an amplitude of about 500 volts (V) to about 5000 V (e.g., between about 1500V to about 3000 V), a pulse width of about 1 microsecond (μs) to about 5 μs for arc-type cavitation or about 1 μs to about 30 μs for corona-type cavitation, and a frequency of about 0.5 Hertz (Hz) to about 5 Hz. In some examples, medical assembly 30 may be configured such that electrical conductors 70A and 70B are independently coupled to energy source 62. In some examples, the intensity of the pressure pulse waves 40 (as shown in FIG. 3A) may be adjusted by controlling the intensity of the electrical signal delivered to primary and secondary electrodes 118 and 120. The intensity of the electrical signal may be function of one or more of a voltage amplitude, a current amplitude, a frequency (e.g., a pulse rate in the case of pulses), a pulse width, or one or more other electrical signal parameters.

Power source 116 delivers operating power to various components of energy source 62. In some examples, power source 116 may represent hard-wired electrical supply of alternating or direct electrical current. In other examples, power source 116 may include a small rechargeable or non-rechargeable battery and a power generation circuit to produce the operating power. Recharging may be accomplished through proximal inductive interaction between an external charger and an inductive charging coil within energy source 62.

A control mechanism 64, such as foot pedal, handheld, or remote-control device, may be connected to energy source 62 to allow the clinician to initiate, terminate and, optionally, adjust various operational characteristics of energy source 62, including, but not limited to, power delivery. Control mechanism 64 can be positioned in a sterile field and operably coupled to the energy source 62 and can be configured to allow the clinician to selectively activate and deactivate the energy delivered between primary and secondary electrodes 118 and 120. In other embodiments, control mechanism 64 may be built into hub portion 54. Control mechanism 64 may, in some examples, control the expansion of expandable member 34.

Figure 9:
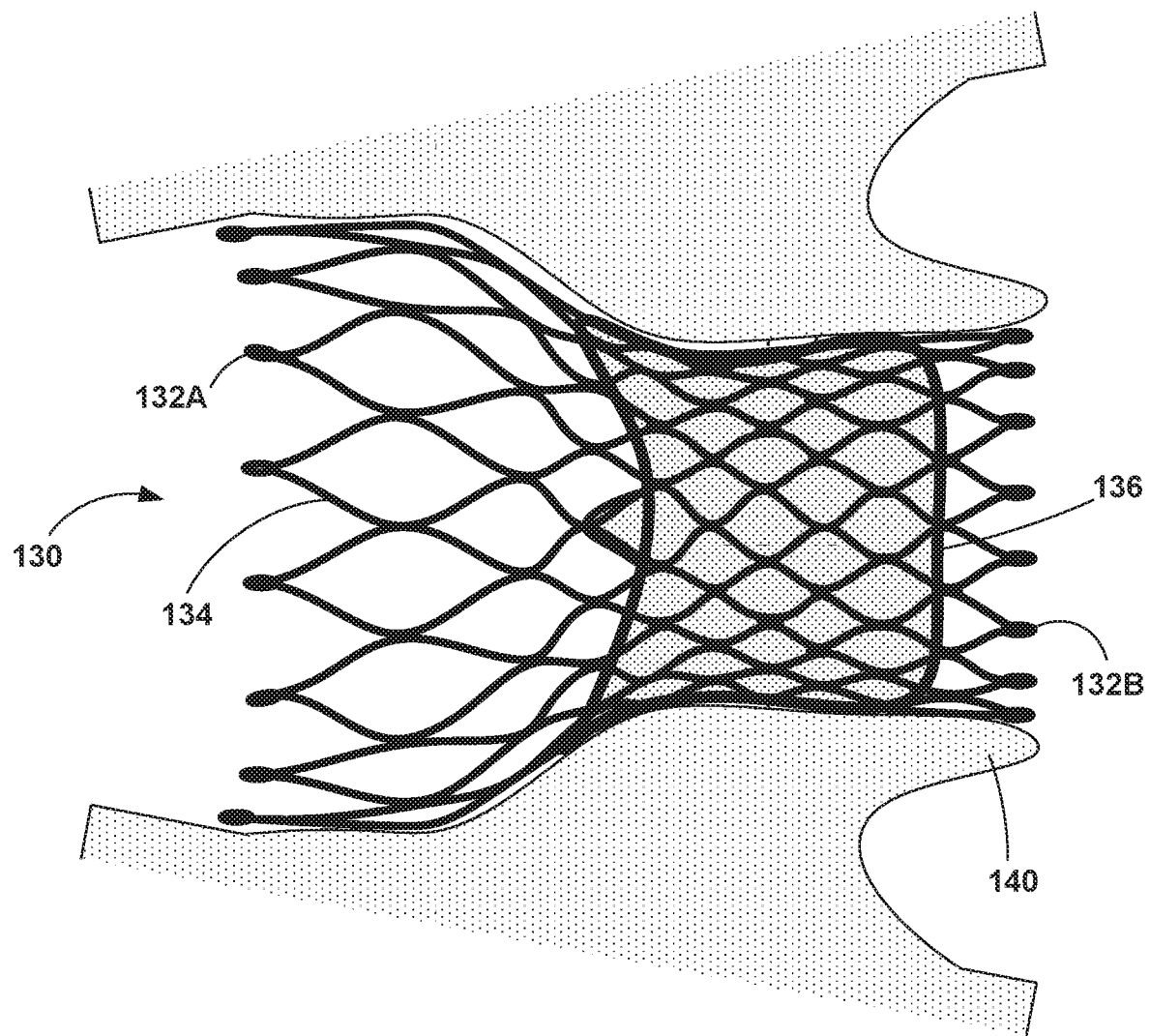
FIG. 9 is a conceptual side view of an example heart valve prosthesis implanted in a heart of a patient.

FIG. 9 is a conceptual side view of an example heart valve prosthesis that may be implanted in a heart of a patient via medical assemblies 12 or 30, for example. As shown in the example of FIG. 9, valve frame 130 is an example heart valve prosthesis in a fully expanded configuration and deployed across native heart valve 140 (e.g., an aortic valve or mitral valve). In some examples, valve frame 130 may include a metallic body comprising a plurality of struts 134 that define any suitable pattern and cell structure (e.g., open cells or closed cells). For example, struts 134 may define a serpentine, zig-zag, or accordion-like pattern. In other examples, struts 134 of valve frame 130 may have other configurations, such as one or more compressible coils. Additionally, or alternatively, valve frame 130 may include a plurality of metallic filaments braided into a tubular body. Valve frame 130 may be delivered through a channel (e.g., channel 36) within an expandable member (e.g., expandable member 34) in a collapsed configuration and then expanded distal of expandable member 34 to be deployed across the heart valve 140. In some examples, valve frame 130 and/or delivery catheters or expandable balloons may be configured to operate with, or be a part of, medical assembly 30. In this manner, valve frame 130 may be implanted after valvuloplasty and/or cavitation.

The metallic body of valve frame 130 may include any suitable metal or metal alloy including, but not limited to nickel titanium alloy, stainless steel, cobalt chromium alloy, or the like. In examples in which valve frame 130 is self-expanding, the metallic body of valve frame 130 may include a shape memory material, such as nitinol.

In such examples, valve frame 130 may include one or more additional components such as an artificial heart valve member 136 (e.g., including valve leaflets), a mounting ring, or the like attached to the body of valve frame 130. As shown in FIG. 9, in examples in which valve frame 130 is part of a heart valve prostheses, valve frame 130 may define a waist that configures valve frame 130 to be positioned within an annulus of native heart valve 140. In some examples, the waist may configure valve frame 130 to self-seat within the annulus of native heart valve 140.

In other examples, valve frame 130 may be used to improve patency in a blood vessel of a patient. In these examples, valve frame 130 may not define a waist, but, rather, may be configured to be more tubular in shape (e.g., a tube defining a constant diameter in the absence of any compressive or expansive forces).

Figure 10:
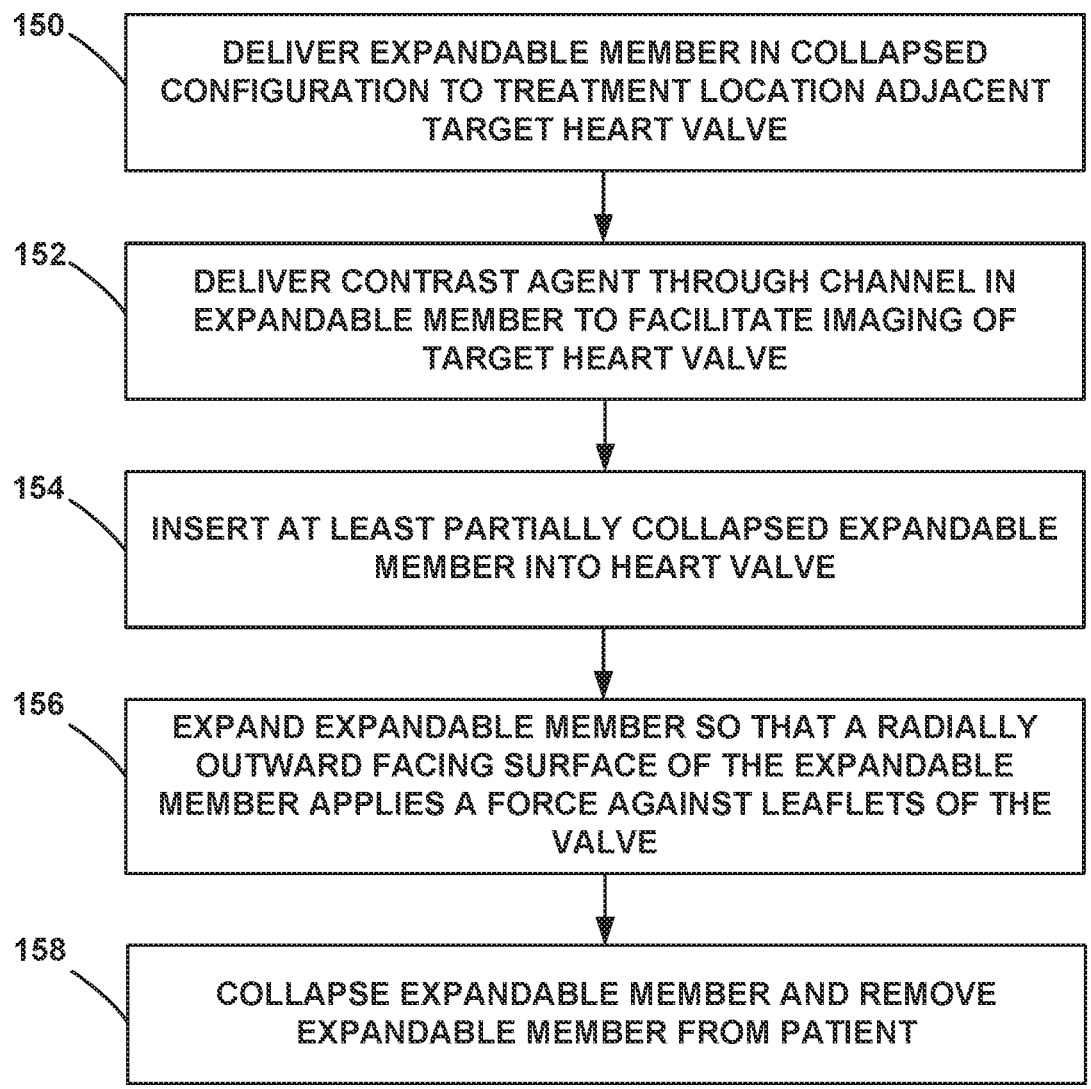
FIG. 10 is a flow diagram of an example technique of expanding an opening of a heart valve using an example medical assembly.
Figure 11:
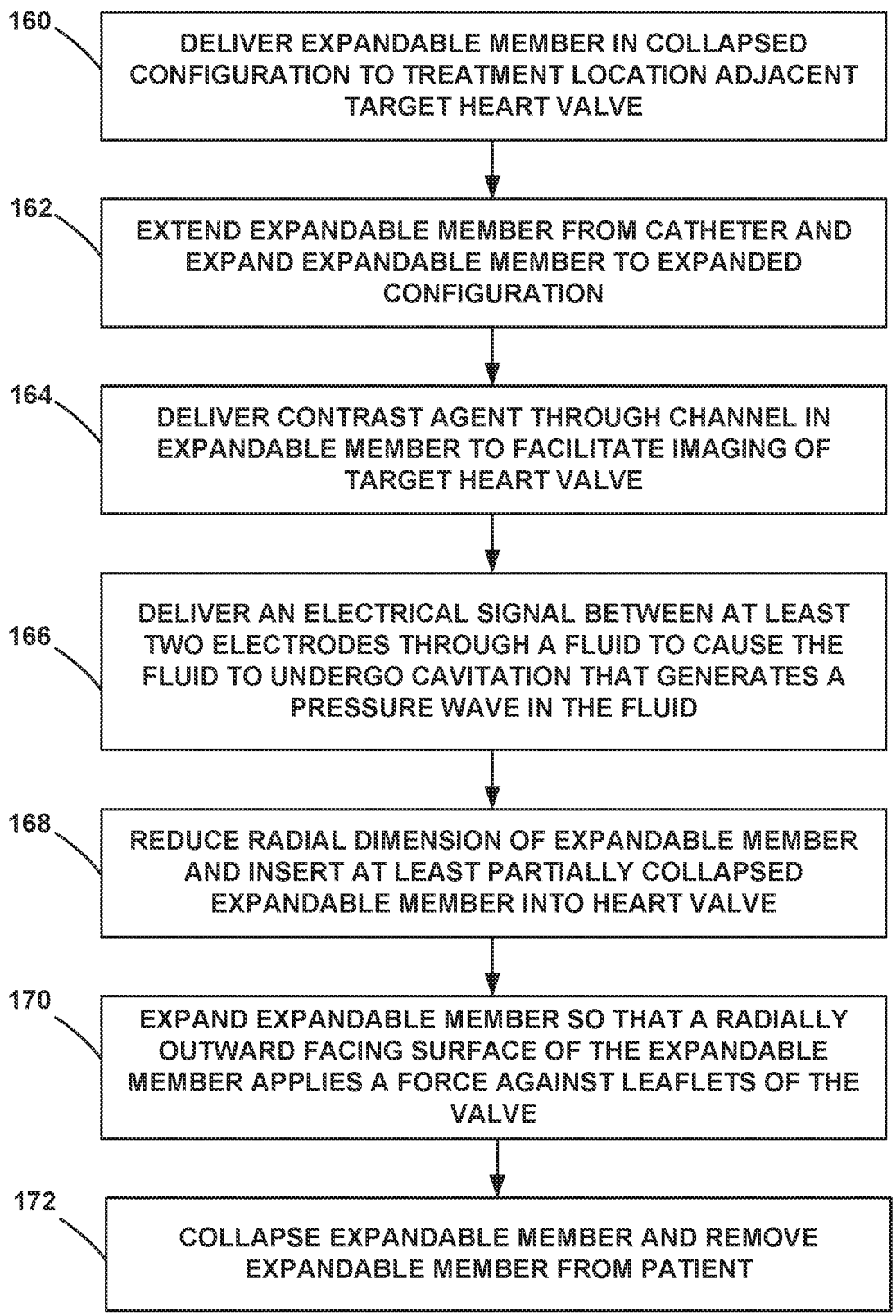
FIG. 11 is a flow diagram of an example technique of providing cavitation therapy using an example medical assembly.

FIG. 10 is a flow diagram of an example technique of expanding an opening of a heart valve using an example medical assembly. For illustrative purposes, the techniques of FIG. 11 are described with reference to the various aspects of medical assembly 12 of FIGS. 2A and 2B; however, such descriptions are not intended to be limiting and the techniques of FIG. 10 may be used with other medical assemblies or using in other procedures.

The technique of FIG. 10 includes delivering expandable member 16 in a collapsed configuration in an inner lumen of catheter 14 as a part of medical assembly 12 to a target treatment location adjacent a target heart valve (150). For example, the target heart valve may be a mitral valve or an aortic valve. Once the expandable member 16 is in position, a clinician may extend expandable member 16 from the distal end of catheter 14 (e.g., by retracting catheter 14) and expand expandable member 16 to at least a partially expanded configuration. In some examples, expandable member 16 may only need to be expanded to the extent necessary to deliver contrast agent out of elongated member 15 and through channel 17. In other examples, expandable member 16 may remain within catheter 14 while contrast agent is delivered through channel 17 and out of elongated member 15.

The clinician may deliver contrast agent through the channel 17 defined by the expandable member 16 to facilitate imaging of the target heart valve (152). For example, the contrast agent may be delivered through an inner elongated member 15, or lumen defined within catheter 14, to a location distal of the distal end of catheter 14 and expandable member 16. Once the target valve is located, or the specific locations of calcified lesions are located, the user may reduce the radial dimension of expandable member 16 (if the expandable member 16 was expanded) and insert the at least partially collapsed expandable member 16 into the heart valve (154). In some examples, expandable member 16 may be fully collapsed and reinserted into catheter 14 in order to be placed within the heart valve. Once expandable member 16 is within the heart valve, the user may again expand expandable member 16 so that a radially outward facing surface of expandable member 16 applies a force against leaflets of the valve (156). This force against the leaflets can be used to increase the opening diameter of the heart valve. The expandable member 16 is then collapsed into the collapsed configuration, reinserted within catheter 14, and the user removes medical assembly 12 from the patient (158).

In some examples, the technique of FIG. 10 may be varied. For example, after opening the valve and prior to collapsing expandable member 16, the user may deliver a heart valve prosthesis to the now opened heart valve through channel 17 defined by expandable member 16. In other examples, fewer or greater steps may be included in the technique of FIG. 10. In this manner, variations on the technique of FIG. 10 may be provided according to the various techniques described herein.

FIG. 11 is a flow diagram of an example technique of providing cavitation therapy using an example medical assembly. For illustrative purposes, the techniques of FIG. 11 are described with reference to the various aspects of the medical assemblies of FIGS. 3A, 3B, 4, 5A, 6A, and 7, however, such descriptions are not intended to be limiting and the techniques of FIG. 11 may be used with other medical assemblies or using in other procedures. The technique of FIG. 11 will be described with respect to medical assembly 30 and energy source 62.

The technique of FIG. 11 includes delivering expandable member 34 in a collapsed configuration in an inner lumen of catheter 32 as a part of medical assembly 30 to a target treatment location adjacent a target heart valve (160). For example, the target heart valve may be a mitral valve or an aortic valve. Once the expandable member 34 is in position, a clinician may extend expandable member 34 from the distal end of catheter 32 (e.g., by pushing inner elongated member 71 and/or retracting catheter 32) and expand expandable member 34 to the expanded configuration (162). Expanding expandable member 34 to a partially or fully expanded state may help to properly position the electrodes relative to the treatment site at the target heart valve. For example, the user may actuate a control that delivers fluid to inflate expandable member 34 to the expanded configuration.

Before or after expanding expandable member 34, the clinician may deliver contrast agent through the channel defined by the expandable member 34 to facilitate imaging of the target heart valve (164). For example, the contrast agent may be delivered through inner elongated member 80, or a tube within inner elongated member 80, to a location distal of the distal end of expandable member 34. Once the target valve is located, or the specific locations of calcified lesions are located and while expandable member 34 is fully or partially expanded within the cardiovasculature, the user may control energy source 62 to deliver an electrical signal between at least two electrodes 35 through a fluid to cause the fluid to undergo cavitation that generates a pressure wave in the fluid (166). Delivery of electrical signals may continue until the calcified lesions are at least partially removed from the heart valve.

As described above, electrodes 35 (e.g., a primary electrode and secondary electrode) may transmit energy to fluid (e.g., electrical energy) that rapidly heats a portion of fluid to produce short-lived gaseous steam/plasma bubbles within the fluid. The steam/plasma bubbles may represent relatively low-pressure pockets of vapor generated from the surrounding fluid. The low-pressure steam/plasma bubbles eventually collapse in on themselves due to the relatively high pressure of the surrounding fluid. As steam/plasma bubbles collapse, the bubbles release a large amount of energy in the form of a high-energy pressure pulse wave within fluid that propagate through fluid where they impact calcified lesions transmitting the mechanical energy of pressure pulse waves into the tissue and calcified lesions. The energy transmitted to calcified lesions may cause the lesions to fracture or break apart.

After the calcified lesions are treated, the user may reduce the radial dimension of expandable member 34 and insert the at least partially collapsed expandable member 34 into the heart valve (168). In some examples, expandable member 34 may be fully collapsed and reinserted into catheter 32 in order to be placed within the heart valve. Once expandable member 34 is within the heart valve, the user may again expand expandable member 34 so that a radially outward facing surface of expandable member 34 (e.g., outer surface 92A) applies a force against leaflets of the valve (170). This force against the leaflets can be used to increase the opening diameter of the heart valve. The expandable member 34 is then collapsed into the collapsed configuration, reinserted within catheter 32, and the user removes medical assembly 30 from the patient 172).

In some examples, the technique of FIG. 11 may be varied. For example, after opening the valve and prior to collapsing expandable member 34, the user may deliver a heart valve prosthesis to the now opened heart valve through channel 36 defined by expandable member 34. In other examples, fewer or greater steps may be included in the technique of FIG. 11. For example, medical assembly may be used to only generate pressure waves via cavitation (166) instead of delivering contrast agent and/or opening the valve (170). In this manner, variations on the technique of FIG. 11 may be provided according to the various techniques described herein.

Figure 12:
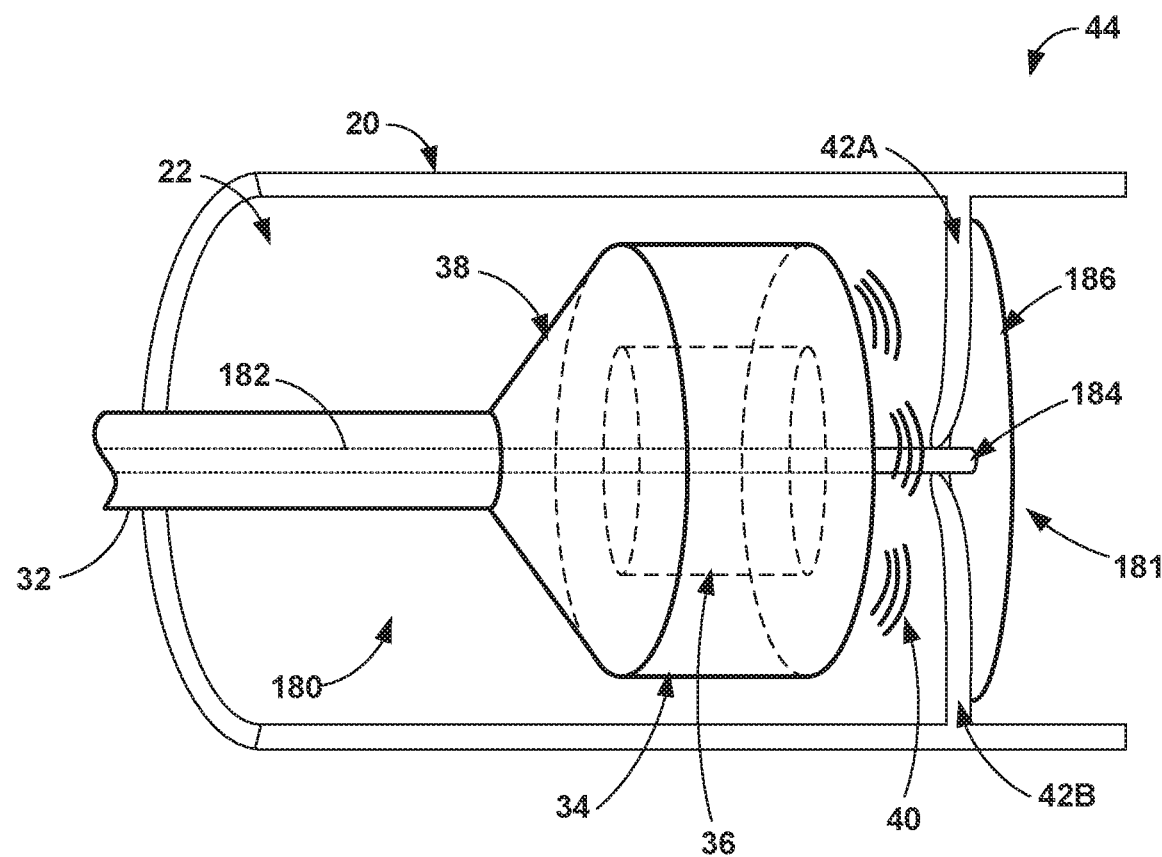
FIG. 12 is a conceptual view of an example medical assembly configured to deliver cavitation therapy to leaflets of a valve and deliver a support structure to an opposing side of the valve.

FIG. 12 is a conceptual view of an example medical assembly 180 configured to deliver cavitation therapy to leaflets of a valve and deliver a support structure to an opposing side of the valve. Medical assembly 180 may be similar to medical assembly 30 of FIG. 3A, but medical assembly 180 may also include support device 181. As shown in the example of FIG. 12, similar to FIG. 3A, aortic valve 24 (shown in FIG. 3A) includes three leaflets (which may include leaflets 42A and 42B) and is disposed upstream from aorta 20.

Electrodes (e.g., electrodes 35) carried by expandable member 34 may be configured to deliver pressure pulse waves 40 toward the leaflets (e.g., leaflets 42A and 42B) of aortic valve 24. However, the pressure pulse waves 40 may cause leaflets 42A and 42B to move within the blood. This movement could cause injury to leaflets 42A and 42B and/or limit the energy of the pressure pulse waves 40 that can fracture or dislodge calcified lesions. Support device 181 may be configured to provide support for the leaflets when pressure pulse waves 40 are delivered to reduce the risk of injury to leaflets 42A and 42B and/or increase efficacy of the pressure pulse waves 40 in fracturing or dislodging calcifications.

Support device 181 may be delivered through a lumen of catheter 32 (e.g., inner lumen 82) and include a shaft 182 and distal portion 184 that is coupled to, or formed as part of, expandable flange 186. Expandable flange 186 may be collapsed within catheter 32, but passed through the valve and expand (e.g., self-expand or via fluid pressure such as within a balloon) on the opposite side of leaflets 42. Expandable flange 186 may thus contact the backside of leaflets 42 and provide a force that maintains the position of leaflets 42 during delivery of the pressure pulse waves 40. This process may improve efficacy of the pressure pulse waves 40 in fracturing or dislodging calcification on leaflets 42. After delivering pressure pulse waves 40, support device 181 may be retracted back within catheter 32 for removal from the patient. Expandable flange 186 may be in the shape of a disk, cylinder, or multiple prongs extending in a radial direction. Expandable flange 186 may be constructed similar to a balloon or a self-expanding polymer or alloy such as nitinol.

Figure 13:
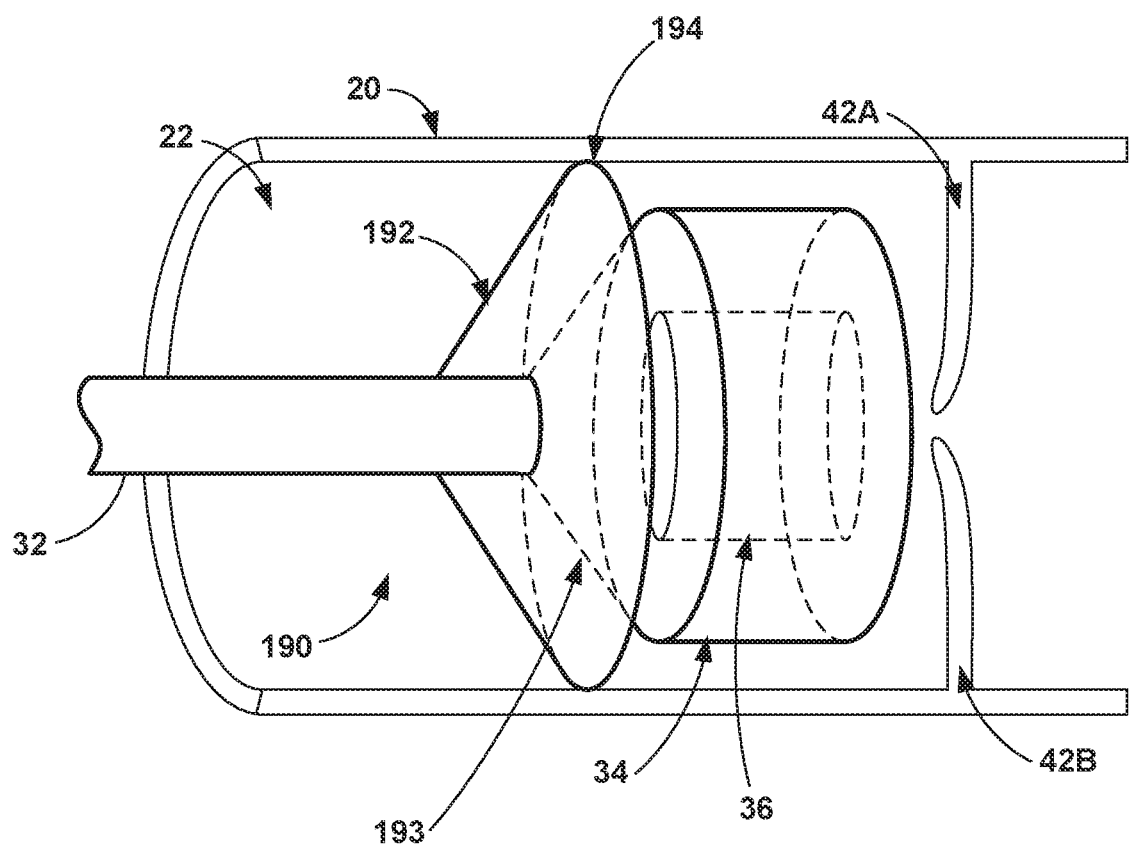
FIG. 13 is a conceptual view of an example medical assembly configured to deliver cavitation therapy to leaflets of a valve that includes a filter configured to contact an inner surface of a vessel.

FIG. 13 is a conceptual view of an example medical assembly configured to deliver cavitation therapy to leaflets of a valve that includes a filter configured to contact an inner surface of a vessel. Medical assembly 190 may be similar to medical assembly 30 of FIG. 3A, but medical assembly 190 includes filter 192 proximal and disconnected from expandable member 34. Filter 192 may be similar to filter 38 of FIG. 3A and described herein. Since filter 192 is not coupled directly to expandable member 34, expandable member 34 may be coupled to catheter 32 and/or a structure within catheter 32 via one or more members 193 (e.g., a conically shaped material or several strands or structures tethering expandable member 34 to catheter 32).

As shown in FIG. 13, filter 192 may be attached to or carried by catheter 32. Filter 192 may be configured to expand radially until the radial edge 194 of filter 192 contacts the interior surface of artery. For example, filter 192 may be constructed to open over a variety of diameters and until radial edge 194 contacts the wall of the aorta. Filter 192 is also disposed proximal of expandable member 34. In this manner, any calcification particles removed from leaflets 42 may be captured by filter 192 and, in some examples, funneled through catheter 32 and out of the patient. Since filter 192 may contact the wall of aorta 20, expandable member 34 may be expanded to a diameter smaller than that of filter 192. This smaller diameter of expandable member 34 may enable the electrodes (e.g., electrodes 35) to be placed at a position with respect to leaflets 42 that facilitates greater removal of calcified deposits. In some examples, expandable member 34 may also be configured to move axially with respect to filter 192, even when filter 192 is deployed such that radial edge 194 is in contact with aorta 20. In addition, since expandable member 34 may not need to contact the wall of aorta 20, expandable member 34 may be constructed of one size that can treat patients with different sized aortas and valves.

Figure 14B:
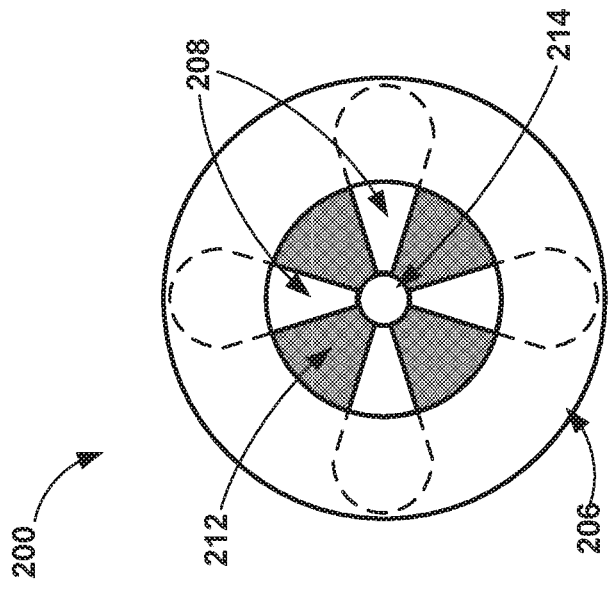
FIGS. 14A and 14B include a conceptual side view and an axial view of an example medical assembly configured to expand within a cardiovascular structure.
Figure 14A:
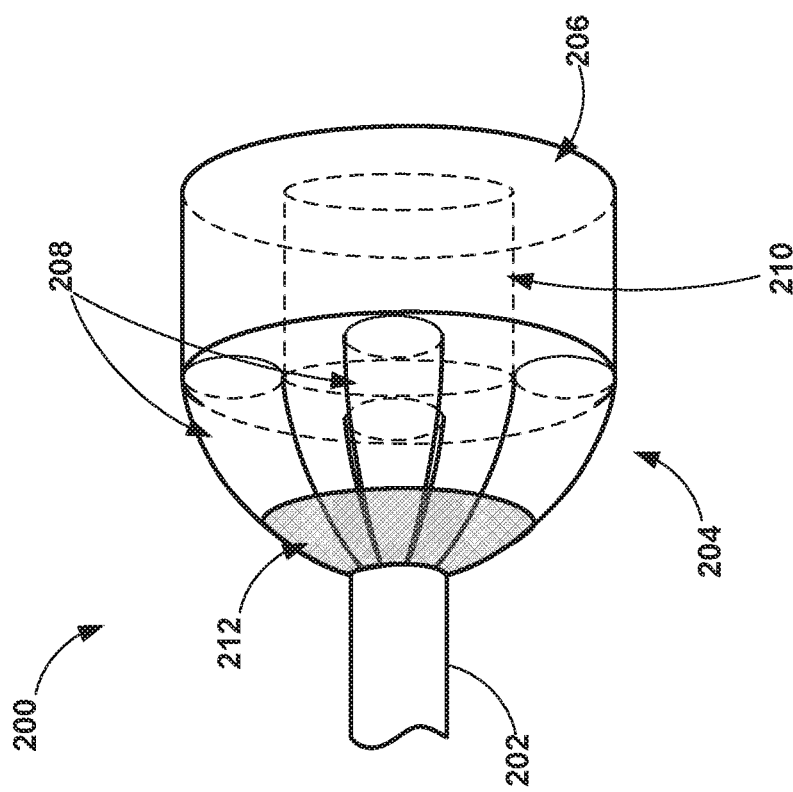

FIGS. 14A and 14B include a conceptual side view and an axial view of an example medical assembly 200 configured to expand within a cardiovascular structure. Medical assembly 200 may be similar to medical assembly 30, but expandable member 204 and filter 212 may be constructed differently than expandable member 34 and filter 38, respectively.

Expandable member 204 may be configured to expand to include a generally toroid structure 206 that defines an inner channel 210, where toroid structure 206 is coupled to connecting members 208. Connecting members 208 may form a tent-like structure that defines passages between each of the connecting members 308. Connecting members 208 may couple toroid structure 206 to catheter 202. Connecting members 208 and toroid structure 206 may form a sealed balloon (e.g., constructed of a polymer) that can be expanded. Connecting members 208 and toroid structure 206 may form a unitary structure in some examples, but in other examples connecting members 208 may be formed of different materials than toroid structure 206 (which may be similar to expandable member 34). In some examples connecting members 208 may be formed from one or more polymer strands or an alloy construction. Although four connecting members 208 are show in FIG. 14A, expandable member 204 may include fewer than four (e.g., two or three) connecting members in some examples, while five, six, seven, eight, or more connecting members may be provided in other examples. Generally connecting members 208 may be circumferentially equidistant from each other, but, in other examples, connecting members 208 may be distributed unevenly around the circumference of expandable member 204.

Filter 212 may be positioned around, and/or between, at least a portion of connecting members 208 in order to capture any debris that may flow downstream in the blood. For example, as shown in FIG. 14B, filter 212 has a diameter at least as large as the diameter of channel 210 in order to capture any debris that passes through channel 210. Debris captured by filter 212 may be funneled into lumen 214 defined by catheter 202. Filter 212 may be constructed of materials similar to filter 38 described herein.

Figure 15B:
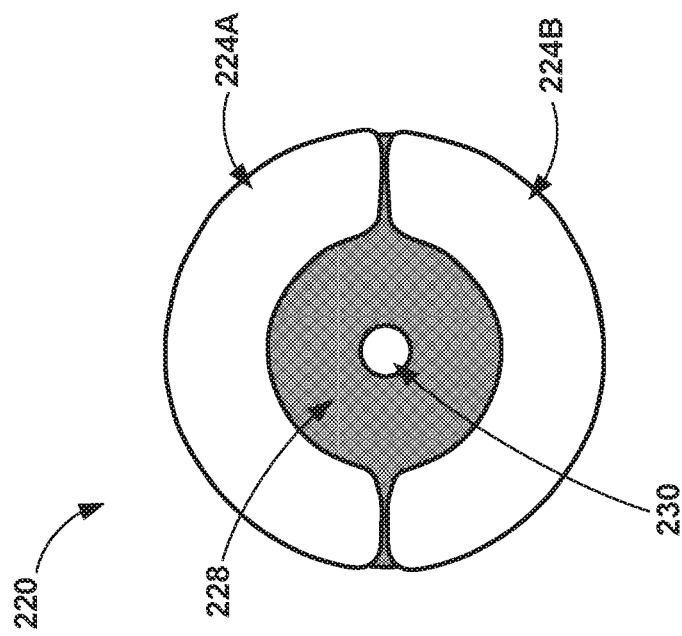
FIGS. 15A and 15B include a conceptual side view and an axial view of an example medical assembly including multiple expandable members configured to expand within a cardiovascular structure.
Figure 15A:
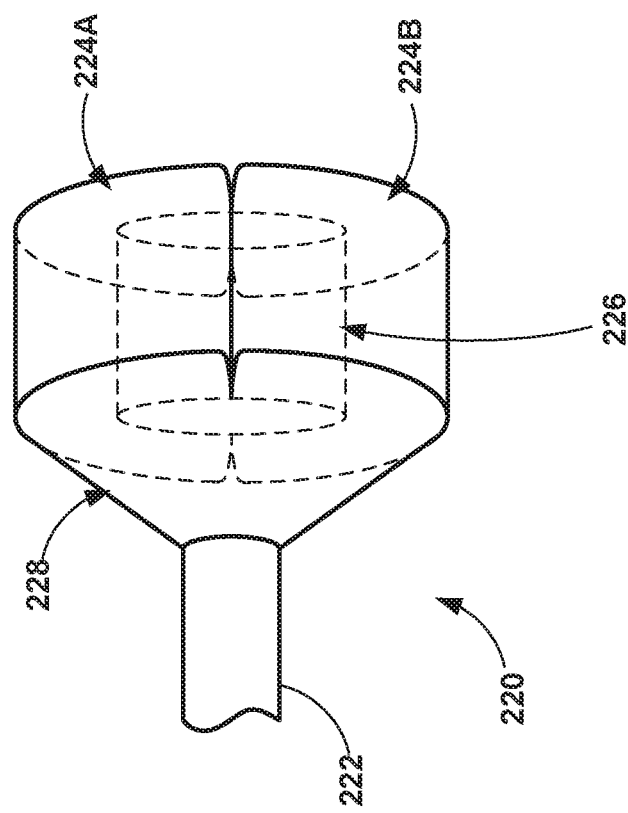

FIGS. 15A and 15B include a conceptual side view and an axial view of an example medical assembly 220 including multiple expandable members 224A and 224B (collectively "expandable members 224") configured to expand within a cardiovascular structure. Medical assembly 200 may be similar to medical assembly 30, but expandable members 224 may together define channel 226 instead of a single structure such as expandable member 34. Filter 228 may be similar to filter 38, but attached to each of expandable members 224.

Expandable members 224 may include two generally be semi-cylindrical shaped members that generally form a toroid shape, and define channel 226, when in the expanded configuration. For example, each of expandable members 224 may be formed as a curved or cupped balloon. Multiple expandable members 224 may facilitate expanding into structures of various sizes of the patient. As shown in FIG. 15B, expandable members 224 may contact each other, but in other examples, there may be a gap between expandable members. Debris that may pass through channel 226 may be captured by filter 228 and funneled into lumen 230 (e.g., similar to lumen 82) of catheter 222. Although two expandable members 224 are shown, three or more expandable members may be provided in other examples. For example, another example of medical assembly 220 may include five separate expandable members (e.g., similar to flower petals) where the expandable members together form a generally toroid shape. One or more electrodes (e.g., electrodes 35) may be disposed at least one, or perhaps all, of the separate expandable members 224. For example, two electrodes of each polarity may be disposed in each expandable member.

In other examples, electrodes of different polarities may be located in different expandable members. In other examples, all electrodes carried by the expandable members may be of the same polarity, where a ground electrode or electrode of opposite polarity is introduced through lumen 230 on a shaft or guidewire.

Although expandable members 224 are shown as being disposed in the same axial location, one or more expandable members 224 may alternatively be disposed at different axial and circumferential locations. For example, a single expandable member 224 may define a spiral shape that forms a channel through the center of the spiral similar to channel 226. The spiral shaped expandable member may make more than one full turn, such as two, three, or four turns. The expandable member may contact itself as each turn is made (e.g., such as a compressed spring), or the expandable member may also define a spiral gap between adjacent portions of the expandable member. A spiral shaped expandable member may be formed as a balloon or a self-expanding material (e.g., nitinol). In some examples, a spiral shaped balloon may also include a self-expanding material that assists in maintaining the spiral shape.

Figure 16B:
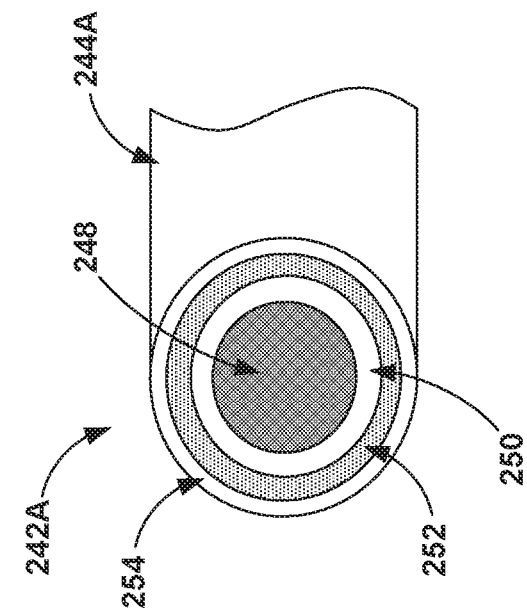
FIGS. 16A and 16B are conceptual views of an electrode configuration to cause a fluid to undergo cavitation.
Figure 16A:
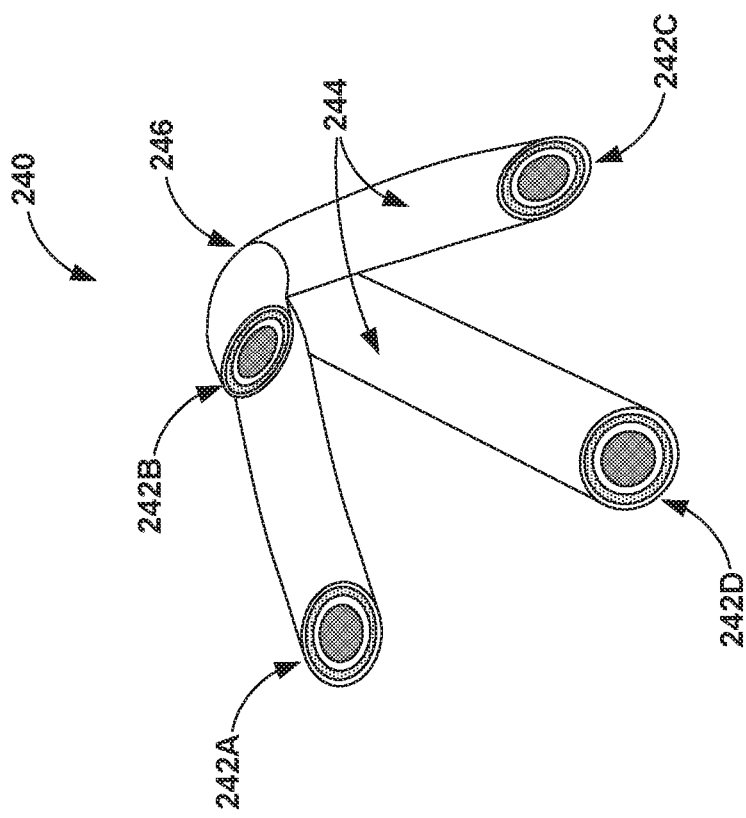

FIGS. 16A and 16B are conceptual views of an electrode configuration 240 to cause a fluid to undergo cavitation. Electrode configuration 240 may be an alternative to concentric electrodes 76 and 78 of FIGS. 6A and 7. For example, one or more of electrode configuration 240 may be at least partially disposed within expandable member 34 and operated to produce cavitation within the fluid surrounding the electrodes at each tip of electrode configuration 240.

As shown in FIG. 16A, electrode configuration 240 is shaped like a "claw" or multiple prongs that includes four electrode tips 242A, 242B, 242C, and 242D (collectively "electrode tips 242") that connect to base 246 via respective arms 244. The exposed surface of each of electrode tips 242 may generally planar, but in some examples, one or more of electrode tips 242 may be concave or convex in other examples. As shown in FIG. 16A, each of electrode tips 242 is tilted slightly towards each other. This tilt may focus cavitation produced pressure waves towards a desired location. Although four electrode tips 242 are shown in the example of FIG. 16A, electrode configuration 240 may include one, two, three, five, or more electrode tips in other examples.

Each of electrode tips 242 exposes distal ends of respective conductors. As shown in FIG. 16B, example electrode tip 242A is shown as including inner electrode 248 and outer electrode 252 separate by insulation 250. Inner electrode 248 may be a solid wire that terminates at electrode tip 242A and outer electrode 242 may be a cylindrical conductor that surrounds inner electrode 248. Insulation 250 may thus be an electrically insulating sleeve disposed between inner electrode 248 and outer electrode 252. Therefore, when inner electrode 248 and outer electrode 252 have opposing polarities, an electrical signal will pass through a fluid contacting each electrode 248 and 252. Insulating sheath 254 may electrically insulate the outer surface of outer electrode 252. In other examples, inner electrode 248 and outer electrode 252 may be coupled to non-coaxial conductors (e.g., side-by-side conductors) within arm 244A. In some examples, electrodes 248 and 252 may be side-by-side electrodes instead of co-axial electrodes as shown in the example of FIG. 16B.

Electrode configuration 240 may by partially disposed within expandable member 34. For example, base 246 may be disposed within expandable member 34 with each of arms 244 extending beyond the distal end of expandable member 34 such that each of electrode tips 242 are disposed external from expandable member 34. In other examples, at least one, or even all, of electrode tips 242 may be disposed within expandable member 34. In examples in which multiple electrode configurations 240 are carried by expandable member 34, each of electrode configurations 240 may be disposed at different circumferential, or angular, positions around the distal, or radial, surface of expandable member 34.

The techniques described in this disclosure may be implemented, at least in part, in hardware, software, firmware or any combination thereof. For example, various aspects of the described techniques may be implemented within one or more processors or processing circuitry, including one or more microprocessors, digital signal processors (DSPs), application specific integrated circuits (ASICs), field programmable gate arrays (FPGAs), graphics processing units (GPUs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, circuits or components may be implemented together or separately as discrete but interoperable logic devices. Depiction of different features as circuits or units is intended to highlight different functional aspects and does not necessarily imply that such circuits or units must be realized by separate hardware or software components. Rather, functionality associated with one or more circuits or units may be performed by separate hardware or software components or integrated within common or separate hardware or software components.

The techniques described in this disclosure may also be embodied or encoded in a computer-readable medium, such as a computer-readable storage medium, containing instructions that may be described as non-transitory media. Instructions embedded or encoded in a computer-readable storage medium may cause a programmable processor, or other processor, to perform the method, e.g. when the instructions are executed. Computer readable storage media may include cloud storage mediums, random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

What is claimed is:

1. A medical assembly comprising:
   first and second expandable members positioned side by side, the first and second expandable members configured to expand from a collapsed configuration to an expanded configuration, the first and second expandable members configured to at least partially define a channel between the first and second expandable members in the expanded configuration;
   a catheter defining a lumen and configured to deliver a first fluid from the lumen and through the channel defined by the first and second expandable members in the expanded configuration, wherein the first and second expandable members are configured to reside within the catheter in the collapsed configuration; and
one or more electrodes configured to transmit an electrical signal through a second fluid adjacent the first and second expandable members to cause the second fluid to undergo cavitation that generates a pressure wave within the second fluid,
wherein the second fluid comprises the first fluid and/or blood in a heart or vasculature of a patient.

2. The medical assembly of claim 1, wherein the one or more electrodes is positioned within one of the first and second expandable members.

3. The medical assembly of claim 1, wherein the one or more electrodes is positioned on one of the first and second expandable members.

4. The medical assembly of claim 1, wherein the channel terminates at a proximal end of the first expandable member.

5. The medical assembly of claim 1, wherein the one or more electrodes includes a plurality of electrodes.

6. The medical assembly of claim 1, further comprising a filter disposed proximal of the first expandable member in the expanded configuration, the filter configured to expand from a collapsed filter configuration to an expanded filter configuration.

7. The medical assembly of claim 6, wherein, in the expanded filter configuration, the filter has a distal filter diameter larger than a proximal filter diameter.

8. A delivery system for treating valvular stenosis comprising:
a catheter having a proximal end and a distal end, and defining a lumen therethrough;
at least one expandable member disposed at the distal end of the catheter and expandable from a collapsed condition to an expanded condition by fluid delivered through the lumen to the at least one expandable member, wherein when in the expanded condition the at least one expandable member defines a channel allowing blood to flow through or past the at least one expandable member;
at least one electrode within the at least one expandable member or on a surface of the at least one expandable member;
an energy source electrically coupled to the at least one electrode for transmitting an electric signal to the at least one electrode when the at least one expandable member is an expanded condition;
wherein when the catheter is delivered to a patient's heart valve and the at least one expandable member is placed across the patient's heart valve and expanded to an expanded condition, the transmitted electric signal generates a pressure wave to act on and treat stenosis of the heart valve.

9. The delivery system of claim 8, wherein the at least one expandable member is an inflatable balloon.

10. The delivery system of claim 9, wherein the at least one electrode is placed inside the inflatable balloon and when the inflatable balloon is inflated with fluid to an expanded condition and an electric signal is transmitted to the at least one electrode, the fluid in the inflated balloon undergoes cavitation that generates the pressure wave.

11. The delivery system of claim 8, wherein the at least one expandable member is a plurality of inflatable balloons.

12. The delivery system of claim 11, wherein the at least one electrode comprises a plurality of electrodes with an electrode placed inside each of the plurality of inflatable balloons and when the inflatable balloons are inflated with fluid to an expanded condition and an electric signal is transmitted to the plurality of electrodes, the fluid in the inflated balloons undergo cavitation that generates pressure waves.

13. The delivery system of claim 8, further comprising a filter attached to the catheter and disposed proximal of the at least one expandable member to capture any fragments generated from treatment of the heart valve stenosis.

14. A method for treating calcified heart valve leaflets comprising the steps of:
advancing a delivery system, having at least one expandable member, through a patient's vasculature to a position at least partially within a calcified heart valve;
expanding the at least one expandable member to apply a force to displace and open the heart valve, wherein the at least one expandable member defines a channel allowing blood to flow through or past the at least one expandable member;
transmitting an electrical signal to the at least one expandable member to generate a pressure wave to disrupt calcification in the calcified heart valve leaflets;
collapsing the at least one expandable member; and
removing the delivery system from the patient.

15. The method of claim 14, wherein the step of expanding the at least one expandable member comprises supplying a fluid to the at least one expandable member.

16. The method of claim 15, wherein the step of transmitting an electrical signal comprises transmitting an electrical signal from an energy source to at least two electrodes on or within the at least one expandable member to cause the fluid to undergo cavitation that generates the pressure wave.

17. The method of claim 16, wherein the step of generating the pressure wave comprises transmitting an electrical signal to the at least two electrodes to generate steam bubbles within the at least one expandable member which subsequently collapse releasing energy in the form of the pressure wave.

18. The method of claim 14, further comprising the step of deploying a filter downstream of the calcified valve to capture and collect emboli or any portions of the calcification dislodged during the steps of treating the calcified heart valve leaflets.

19. The method of claim 14, wherein the step of advancing the delivery system includes the further step of positioning the at least one expandable member downstream of the calcified heart valve leaflets and directing the pressure wave upstream toward the calcified heart valve leaflets.

* * * * *